United States Patent
Windham et al.

(10) Patent No.: US 6,587,575 B1
(45) Date of Patent: Jul. 1, 2003

(54) METHOD AND SYSTEM FOR CONTAMINANT DETECTION DURING FOOD PROCESSING

(75) Inventors: William R. Windham, Watkinsville, GA (US); Kurt C. Lawrence, Watkinsville, GA (US); Bosoon Park, Bogart, GA (US); Luis A. Martinez, Kenner, LA (US); Mark A. Lanoue, Long Beach, MS (US); David A. Smith, Ocean Springs, MS (US); Jerry Heitschmidt, Slidell, LA (US); Gavin H. Poole, Slidell, LA (US)

(73) Assignees: The United States of America as represented by the Secretary of Agriculture, Washington, DC (US); University of Georgia Research Foundation, Inc., Athens, GA (US); ProVision Technologies Division Institute for Technology Development, Stennis Space Center, MS (US)

( * ) Notice: Subject to any disclaimer, the term of this patent is extended or adjusted under 35 U.S.C. 154(b) by 15 days.

(21) Appl. No.: 09/779,832

(22) Filed: Feb. 9, 2001

(51) Int. Cl.⁷ .................................................. G06K 9/00
(52) U.S. Cl. ..................................... 382/110; 250/458.1
(58) Field of Search .................... 382/110; 250/458.1, 250/461.2, 339.09; 435/34

(56) References Cited

U.S. PATENT DOCUMENTS

| | | | |
|---|---|---|---|
| 4,631,413 A | * 12/1986 | Jensen et al. ............ 250/458.1 |
| 5,239,180 A | * 8/1993 | Clarke .................. 250/339.11 |
| 5,488,479 A | 1/1996 | Williams et al. |
| 5,621,215 A | 4/1997 | Waldroup et al. |
| 5,760,406 A | * 6/1998 | Powers .................... 250/459.1 |
| 5,821,546 A | 10/1998 | Xiao et al. |
| 5,914,247 A | 6/1999 | Casey et al. |
| 6,114,699 A | 9/2000 | Barton et al. |

OTHER PUBLICATIONS

Lumia Et Al., Texture Analysis of Aerial Photographs, Pattern Recognition, vol. 16, pp. 39–46, 1983, Perganom Press Ltd., Great Britain.

Williams, P.C., Commercial Near–Infrared Reflectance Analyzers, In: Williams et al, eds., Near Infrared Technology in the Agricultural and Food Industries, American Association of Cereal Chem., St. Paul, MN., pp. 107–142, 1987.

Miller Et Al., A Color Vision System for Peach Grading, Transactions of the ASAE, vol. 32(4), Jul.–Aug. , 1989, 1484–1490.

Meyer Et Al., Leaf Nitrogen Analysis of Poinsettia (Euphorbia Pulcherrima Will D.) Using Spectral Properties in Natural and Controlled Lighting, Applied Engineering in Agriculture, vol. 8(5), 715–722, 1992.

Ni Et Al., An Automated Corn Kernal Inspection System Using Machine Vision, American Society of Agricultural Engineers, Paper No. 933032, Jun. 1–8, 1993.

Park Et Al., Multilspectral Image Textural Analysis for Poultry Carcasses Inspection, American Society of Agricultural Engineers, Paper No. 946027, 1–16, 1994.

Steinmetz Et Al, Sorting Cut Roses with Machine Vision, Transactions of the ASAE, vol. 37(4)1347–1353, 1994.

(List continued on next page.)

Primary Examiner—Leo Boudreau
Assistant Examiner—Barry Choobin
(74) Attorney, Agent, or Firm—M. Howard Silverstein; John D. Fado; Gail E. Poulos

(57) ABSTRACT

Imaging systems, containing at least one charge-coupled device detector, are used for determining contamination of foodstuffs, such as for example, animal carcasses. Image processing algorithms allow for the identification of contaminants.

21 Claims, 14 Drawing Sheets

(3 of 14 Drawing Sheet(s) Filed in Color)

Microfiche Appendix Included
(1 Microfiche, 71 Pages)

OTHER PUBLICATIONS

Transactions of the ASAE, vol. 37(6), 1983–1988, Nov./Dec., 1994.

Tao Et Al., Machine Vision for Color Inspection of Potatoes and Apples, Transactions of the ASAE, vol. 38(5), 1555–1561, 1995.

* cited by examiner

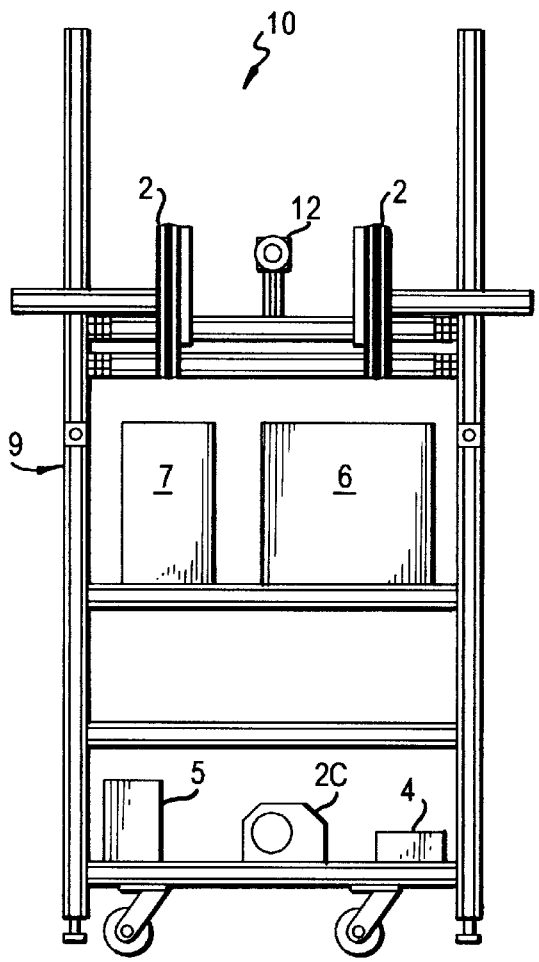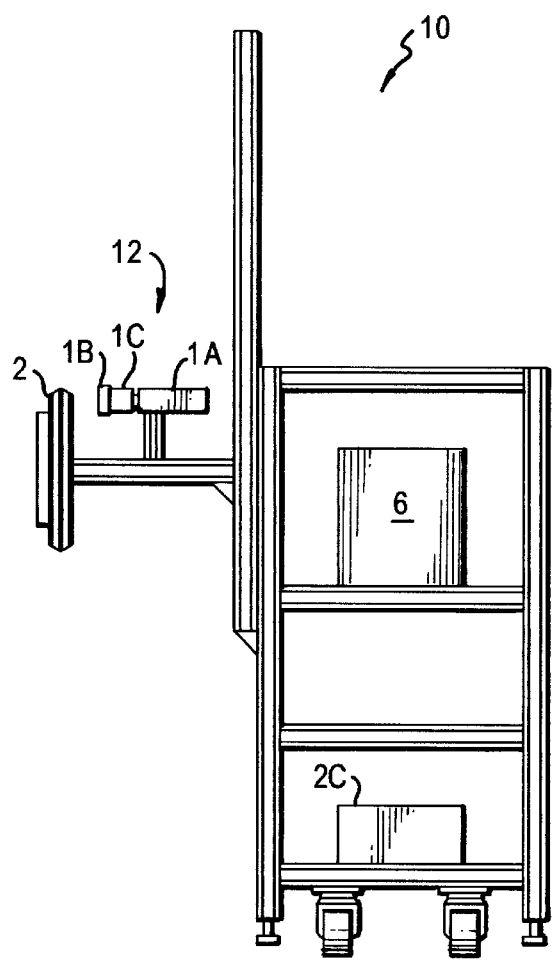
FIG. 1A
FIG. 1B
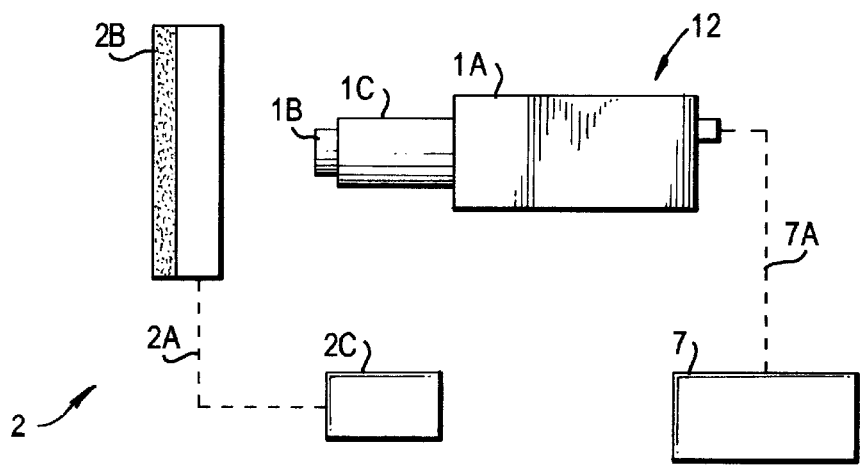
FIG. 1C

| 1 | 3 | 5 | 1 | 3 | 9 |
|---|---|---|---|---|---|
| 4 | 1 | 9 | 0 | 1 | 4 |
| 6 | 1 | 8 | 1 | 5 | 7 | a, b, c

| | | | | | |
|---|---|---|---|---|---|
| | 4.2 | 3.2 | 3.7 | | |

MEAN

FIG.4A

| 1 | 3 | 5 | 1 | 3 | 9 |
|---|---|---|---|---|---|
| 4 | 1 | 9 | 0 | 1 | 4 |
| 6 | 1 | 8 | 1 | 5 | 7 | a, b, c

| | | | | | |
|---|---|---|---|---|---|
| | 9.2 | 11.2 | 10.8 | | |

VARIANCE

FIG.4B

Composite Color (Red: 634 nm; Green: 520 nm; Blue: 446 nm)

434 nm

517nm 565 nm 628 nm

517/434 nm

565/434 nm

628/434 nm

565/517 nm

628/517 nm

628/565 nm

METHOD AND SYSTEM FOR CONTAMINANT DETECTION DURING FOOD PROCESSING

MICROFICHE APPENDIX

A Microfiche Appendix containing 1 Microfiche containing 71 frames is included.

BACKGROUND OF THE INVENTION

1. Field of the Invention

The invention relates to imaging systems for detecting contamination on foods. The imaging systems can be used, for example, for real-time detection of fecal and ingesta on meat and poultry carcasses which may be present when carcasses are being processed. The systems include both hyperspectral and multispectral imaging systems including apparatus, methods, and computer readable mediums.

2. Description of the Related Art

Microbial pathogens in food cause an estimated 76 million cases of human illnesses and up to 5,000 deaths annually, according to the Center for Disease Control and Prevention (Mead et al. Emerging Infectious Diseases 5(5) 607–625, 1999). In 1996, the USDA Economic Research Service reported that the annual cost of the food-borne illnesses caused by six common bacterial pathogens: Campylobacter spp., *Clostridium perfringens, Escherichia coli* O157:H7, Listeria monocytogenes, Salmonella spp., and *Staphylococcus aureus*; ranges from 2.9 billion to 6.7 billion dollars. The foods most likely to cause these illnesses are animal products such as red meat, poultry and eggs, seafood, and dairy products.

Contamination of meat and poultry in particular, with many bacterial food-borne pathogens, can occur as a result of exposure of the animal carcass to ingesta and/or fecal material during or after slaughter. Accordingly, in order to minimize the likelihood of such contamination, it has been necessary to examine each food item individually to detect the presence of contaminants. Historically, such inspection has been performed visually by U.S.D.A. inspectors, who examine each individual food item as it passes through the processing system.

With poultry, for example, in a modern poultry processing plant, carcasses are placed on shackles of a processing line conveyor system for dressing and inspection. Typically, such conveyors operate at speeds of up to 140 carcasses per minute, with a six inch separation between shackles holding carcasses. Even with multiple inspectors continuously performing such inspection, as little as two seconds are allotted for the inspection of each carcass.

During this inspection period, the inspector is required to check for evidence of eight different diseases as well as for certain quality characteristics, to verify that the chicken was alive when placed on the production line, and to check for evidence of ingesta or fecal contamination. Moreover, during a typical business day operating in two eight hour shifts, a productive poultry processing plant may produce as many as 250,000 processed chickens.

After slaughter, each carcass is examined for disease or evidence of contamination that would render all or part of the carcass unfit for human consumption. Currently the meat processing industry relies upon a variety of methods for the inspection of animal carcasses. These methods typically include human visual inspection, microbiological culture analysis, bioluminescent ATP-based assays, and antibody-based microbiological tests. Unfortunately, these procedures are labor intensive, time consuming, and do not meet the needs of the meat processing industry for an accurate high speed, non-invasive method that is amenable to inspection and real-time analysis.

It is apparent from this brief description that the historical inspection of meat carcases by human inspectors is problematic, and that it is poorly suited to the effective detection and elimination of contaminants in modern poultry processing plants. In particular, it requires the inspectors to make a subjective determination repeatedly. Such a system is prone to errors, which can lead to the entry of contaminated poultry products into the commercial distribution system.

In 1994, the Food Safety Inspection Service (FSIS) published a proposed rule, "Enhanced Poultry Inspection" (USDA, Proposed Rule, Fed. Reg. Volume 59, 35659, 1994) to clarify and strengthen the FSIS's zero-tolerance policy for visible fecal contamination on poultry carcasses. Prior to this rule, FSIS ensured removal of all visible fecal contamination subsequent to postmortem inspection through off-line reinspection, direct on-line observations by an inspector, and application of finished product standards (FPS). Any bird found to be contaminated with feces was set aside for rework or condemnation. The proposed Enhanced Poultry Inspection rule removed "feces" from the list of defects in the FPS.

Since the proposed rule was published, FSIS has adopted the Pathogen Reduction; Hazard Analysis and Critical Control Points (HACCP) Systems (USDA, Final Rule, Fed. Reg., Volume 61, 28805–38855, 1996). The Pathogen Reduction/HACCP system superceded the provisions of the Enhanced Poultry Inspection rule. However, FSIS determined that the zero fecal tolerance provision would complement the Pathogen Reduction/HACCP regulations. Therefore, FSIS finalized the zero fecal tolerance provision of the Enhanced Poultry Inspection proposal (USDA, Final Rule, Fed. Reg., Volume 62, 5139–5143, 1997).

The HACCP regulations require meat processing establishments to identify all food safety hazards likely to occur in a specific process, and to identify critical control points adequate to prevent them. Zero tolerance for visible fecal contamination is a standard that has been implemented by FSIS, forcing poultry processing plants to adopt some point in the evisceration process as a critical control point under HACCP regulations which can be achieved by control, and therefore, is consistent with the HACCP framework. If evisceration machinery is not adjusted properly, the digestive tract of the bird may be torn during evisceration and its contents may leak onto the carcass. In meat processing establishments, fecal contamination of carcasses is a food safety hazard because of its link to microbiological contamination and food borne illness (USDA, 1997, supra). Pathogens may reside in fecal material and ingesta, both within the gastrointestinal tract and on the exterior surface of animals going to slaughter. Therefore, without proper procedures during slaughter and processing, the edible portions of the carcass can become contaminated with bacteria capable of causing illness in humans. Preventing carcasses with visible fecal and ingesta contamination from entering the chlorinated ice water bath (chiller) is critical for preventing cross-contamination of other carcasses. Thus, the final carcass wash, before entering the chiller, has been adopted by many poultry processors as a HACCP system critical control point for preventing cross-contamination of other carcasses.

Compliance with zero tolerance in meat processing establishments is currently verified by visual observation. Three criteria are used for identifying fecal contamination (USDA, 1997, supra). These are color, consistency, and composition. In general, fecal material color ranges from varying shades of yellow to green, brown and white; the consistency of feces is usually semi-solid to paste; and the composition of feces may include plant material. Inspectors use these guidelines to verify that establishments prevent carcasses with visible fecal contamination from entering the chillers. me Visual inspection is both labor intensive and prone to both human error and variability. In addition, there has been a dramatic increase in water usage in most plants as a result of the zero-tolerance fecal standard. Plants have nearly doubled their previous water usage and nationwide the usage has increased an estimated 2 billion gallons (Jones, Poultry, Volume 6, 38–41, 1999).

Efforts have been made to develop automated or semiautomated visual inspection systems for detecting the presence of contaminants on food products during processing. Most systems utilize a technique in which the food item is irradiated with light having a frequency, for example, in the UV range, such that it causes the emission of fluorescent radiation upon striking fecal matter or ingesta. Fluorescent light emanating from the target food item is then measured and compared with a threshold value. If the light gathered exceeds the threshold, a signal indicative of the presence of fecal contamination or ingesta is generated. Such a system is disclosed for example in U.S. Pat. Nos. 5,621,215 and 5,895,921 to Waldroup et al., and U.S. Pat. No. 5,821,546 to Xiao et al.

U.S. Pat. No. 5,914,247 to Casey et al. discloses a fecal and ingesta contamination detection system which is based on the premise that the emission of fluorescent light having a wavelength between about 660 and 680 nm is indicative of the presence of ingesta or fecal material. Thus, carcases being processed are illuminated with UV or visible light (suitable wavelengths being between 300 and 600 nm) and the illuminated surface is then examined for the emission of fluorescent light in the 660 and 680 range. In a preferred embodiment, the intensity of such fluorescence in the 660–680 nm range is compared with that in the 600–620 range as a baseline in order to distinguish fluorescent light emissions of the carcasses themselves.

Visible and near-infrared reflectance (Vis/NIR) spectroscopy is a technique that can be used to detect contamination on foodstuffs. It is a nonconsumptive, instrumental method for fast, accurate, and precise evaluation of the chemical composition of agricultural materials (Williams, Commercial near-infrared reflectance analyzers. In Williams and Norris, eds., Near Infrared Technology in the Agricultural and Food Industries, Am. Assoc. Cereal Chem., St. Paul, Minn., 1987, pp. 107–142). The use of Vis/NIR spectroscopic techniques for classifying wholesome, septicemic, and cadaver carcasses have been reported by Chen and Massie (ASAE, Volume 36(3), 863–889, 1993) and Chen et al. (Appl. Spectrosc., Volume 50, 910–916, 1996b). These studies were conducted with a near-infrared reflectance (NIR) probe in contact with a stationary carcass. More recently, Chen and Hruschka (ASAE Paper No. 983047, American Society of Agricultural Engineers, St. Joseph, Mich., 1999) disclosed an on-line transportable Vis/NIR system (400 to 1700 nm) in which the probe was not in contact with the carcass and carcasses were moving at rates of either 60 or 90 birds per minute. Carcasses were classified as wholesome or unwholesome with an average accuracy of 94% and 97.5% when measured in room light and in the dark, respectively. On-line trials were conducted in a slaughter establishment where spectra of normal and abnormal carcasses were measured. The Vis/NIR system measured carcasses at a rate of 70 birds per minute and was able to classify the carcasses from the spectral data with a success rate of 95% (Chen and Hruschka, 1998, supra). The Vis/NIR method showed promise for separation of wholesome and unwholesome carcasses in a partially automated system. The use of the technique to detect fecal and ingesta surface contaminants on poultry carcasses has not been attempted in the processing plant.

Machine vision is a technology for automating production processes with vision capabilities. Even though machine vision has evolved into a promising technology for many agricultural product applications, such as grading or inspection, there are many factors to be considered in on-line applications: processing speed, reliability, and applicability for industrial environments (Sakar and Wolfe, Trans. ASAE, Volume 28(3), 970–979, 1985; Miller and Delwiche, Trans. ASAE, Volume 32(4), 1484–1490, 1989; Tao et al., Trans. ASAE Volume 38(5), 1555–1561, 1995; Steinmetz et al., Trans. ASAE, Volume 37(4), 1347–1353, 1994; Ni et al., ASAE Paper No. 933032, American Society of Agricultural Engineers, St. Joseph, Mich., 1993; Daley et al., Proc. SPIE, Volume 2345, 403–411, 1994). Image processing techniques have made machine vision research possible to identify and classify agricultural commodities in the spatial domain (Guyer et al., Trans. ASAE, Volume 29(6), 863–869, 1986) as well as in the spectral domain (Meyer et al., Applied Engineering in Agriculture, Volume 8(5), 715–722, 1992).

Machine vision techniques are feasible for grading and parts identification in poultry production (Daley et al., Proceedings of Robotics and Vision '88, Society of Manufacturing Engineers, Dearborn, Mich., 1988). Techniques for recognizing global or systemic defects on poultry carcasses with a color imaging system were reported by Daley et al. (1994, supra ) and Chin et al. (Experimental evaluation of neural networks for inspection of chickens. Research Report of Georgia Tech. Research Institute, 1993). However, this approach had a 90% accuracy for global defect classification and only a 60% accuracy for local defect classification (Daley and Carey, Color machine vision for defect detection: Algorithms and techniques, RIA International Robots and Vision Conf., 1991). Even though a color imaging system has the ability to extract the salient image features, this system was not successful for totally automated inspection because of low accuracy (Daley, Color machine vision for industrial inspection advances and potential for the future, Research Report of Georgia Tech. Research Institute, 1992).

Multispectral imaging technology has potential for food inspection application. Since biological materials at different conditions have different spectral reflectance characteristics, the status of materials could be identified based on their spectral images by selecting optimum wavelengths. Several spectral image processing algorithms have been developed to differentiate wholesome carcasses from unwholesome carcasses (Park and Chen, ASAE Paper No. 946027, American Society of Agricultural Engineers, St. Joseph, Mich., 1994a; Park et al., Trans. ASAE, Volume 39(5), 1933–1941, 1996a). Use of intensities, recorded in different spectral bands of a multispectral camera for segmentation, was effective for classification of poultry carcasses (Park and Chen, Trans. ASAE, Volume 37(6), 1983–1988, 1994b; Park et al., 1996a, supra). Multispectral imaging was used for detecting unwholesome conditions, such as septicemia, cadaver, bruise, tumor, air-sacculitis, and ascites, in poultry carcasses (Park et al., 1996a, supra). Park and Chen (1994b, supra) developed a prototype multispectral imaging system for detecting abnormal poultry carcasses, specifically, to determine the optimal wavelengths of multispectral filters for discerning septicemic and cadaver carcasses from normal carcasses, and to develop a discriminate function for separation of the abnormal carcasses with an accuracy of 93% for normal, 83% for septicemic, and 97% for cadaver carcasses.

Textural feature analysis of multispectral images has potential to discriminate wholesome carcasses from septicemic and cadaver carcasses with high classification accuracy of about 94% (Park and Chen, Trans. ASAE, Volume 39(4), 1485–1491, 1996). However, texture feature analysis would not be useful for an on-line system because of heavy computing time. To achieve real-time processing and analyzing of multispectral gray-scale images for on-line separation of septicemic, cadaver, tumorous, bruised, and other damaged carcasses from the wholesome carcasses, a neural network algorithm was found to be useful (Park et al., ASAE Paper No. 983070, American Society of Agricultural Engineers, St. Joseph, Mich., 1998b). Thus, image texture analysis is an important process in scene analysis because it partitions an image into meaningful regions. Lumia et al., (Pattern Recognition, Volume 16(1), 39–46,1983) described a method for discriminating texture classes based on the measurements of small regions determined by an initial segmentation of the image for categorizing homogeneous regions. Park and Chen (1996, supra) have reported that textural feature analysis of multispectral images containing Vis/NIR wavelengths based on co-occurrence matrices was feasible for discriminating abnormal from normal poultry carcasses at 542 nm.

Development of high speed and reliable inspection systems to ensure safe production of poultry processing has become an important issue. Two dual-wavelength vision systems were developed for on-line machine vision inspection of poultry carcasses (Chao et al., ASAE Paper No. 993118, American Society of Agricultural Engineers, St. Joseph, Mich., 1999). A real-time multispectral image processing algorithm was developed from neural network models with different learning rules and transfer functions for on-line poultry carcass inspection (Park et al., Journal of Agricultural Engineering Research, Volume 69, 351–363, 1998c). The classification accuracy with dual-wavelength spectral images was much higher than single wavelength spectral images in identifying unwholesome poultry carcasses (Chao et al., 1999, supra). Object-oriented software was developed for on-line image capture, off-line development of classification models, and on-line prediction of wholesome and unwholesome carcasses.

An extension of multispectral imaging is known as hyperspectral imaging which is also referred to as imaging spectrometry. Whereas multispectral imaging consists of measurements from two to about ten discrete wavelengths for a given image, hyperspectral imaging measures more than ten contiguous wavelengths, often many more. Like multispectral imaging, hyperspectral imaging is an imaging technique that combines aspects of conventional imaging with spectrometry and radiometry. The result is a technique that is capable of providing an absolute radiometric measurement over a contiguous spectral range for each and every pixel of an image. Thus, data from a hyperspectral image contains two-dimensional spatial information plus spectral information over the spatial image. These data can be considered as a three-dimensional hypercube which can provide physical and geometric observations of size, dimension, orientation, shape, color, and texture, as well as chemical/molecular information such as water, fat, proteins, and other hydrogen-bonded constituent as described above in other Vis/NIR research. Hyperspectral imaging is often used in remote sensing applications (Schowengerdt, The nature of remote sensing, In Remote sensing: Models and methods for image processing, San Diego, Academic Press, 1997, pp. 1–33), but is also being utilized in medical, biological, agricultural, and industrial areas as well (Lu and Chen, SPIE, Volume 3544, 121–133, 1998; Heitschmidt et al., SPIE, Volume 3544, 134–137, 1998; Levenson et al., SPIE, Volume 3438, 300–312, 1998; Lu et al., ASAE Paper No.993120, American Society of Agricultural Engineers, St. Joseph, Mich., 1999; Willoughby et al., SPIE, Volume 2599, 264–272, 1996).

Since the detectors used to measure hyperspectral data are two-dimensional focal plane arrays (FPA), while hyperspectral data are three-dimensional, there must be a technique to collect all the data. The two primary techniques for collecting hyperspectral images are collecting two-dimensional spatial images while sequentially varying a narrow bandwidth of incident energy, or collecting full spectral information of a line-scan image while sequentially varying the position of the line scan (Wolfe, Introduction to imaging spectrometers, SPIE Optical Engineering Press, Bellingham, Wash., 1997; Fisher et al., SPIE, Volume 3438, 23–30, 1998; Hart and Slough, SPIE, Volume 3389, 139–149, 1998). The first technique can typically be demonstrated with either an acousto-optic tunable filter (AOTF) or a liquid-crystal tunable filter (LCTF) in front of a FPA where a two-dimensional spatial image is captured at successive wavelengths. The latter technique is usually implemented in remote sensing as either a push-broom or whisk-broom scanner where a line-scan spectrometer is positioned in front of the FPA so that the FPA successively captures one spatial dimension and one spectral dimension as the scanner or image travels normal to the line-scan direction (first spatial dimension). With each technique, the successive images must be combined to build a hypercube of data for a given image. Each technique has advantages and disadvantages that dictate their use in varying applications. LCTF and AOTF systems can rapidly collect images at discrete wavelengths, which can be easily varied. However, they are better suited for stationary objects to avoid image shifting between discrete wavelength measurements. Push-broom and whisk-broom systems are better suited for moving objects but cannot measure at discrete wavelengths.

Hyperspectral imaging has recently been used to explore the feasibility of detecting defects and contaminants in poultry carcasses (Lu and Chen, 1998, supra; Heitschmidt et al., 1998, supra). Lu et al. (1999, supra) demonstrated that taking a second-derivative of the reflectance value could qualitatively distinguish between four normal carcasses and four cadaver, four septicemia, and three tumorous carcasses. Heitschmidt et al. (1998, supra) contaminated two carcasses with fecal material and were able to qualitatively identify the contaminants with principal component analysis (PCA). However, the time required to perform the PCA was over 40 minutes for a single carcass. Image ratios (wavelength ratios) were also examined. No specific wavelengths were identified as significant for detecting fecal contamination with the limited sample population.

Hyperspectral imaging is an extremely useful tool to throughly analyze the spectra of inhomogeneous materials that contain a wide range of spectral information. It can be an effective technique for identifying surface contaminant on poultry carcasses. At the current time though, it is not suitable for on-line identification of fecal contamination because of lengthy image acquisition and processing times.

SUMMARY OF THE INVENTION

It is therefore, an object of the present invention to provide imaging systems and methods for detecting contamination on foods.

Another object of the present invention is to provide improved processes and apparatus for detection of contamination on a food item, which achieves enhanced accuracy and dependability in positively identifying contaminants.

Another object of the present invention is to provide processes and apparatus which can reliably detect contaminants at a speed which is compatible with the rate at which a food is processed on a production line.

A still further object of the present invention is to provide real-time automated food inspection systems which can quickly and accurately identify contaminated food items in a food processing line.

This and other objects and advantages are achieved by the imaging systems according to the invention, in which digital imaging sensors, such as multispectral or hyperspectral imaging camera units are used to collect reflectance data from a food source on which contamination is to be detected. Reflectance data gathered by the imaging system are then processed in a digital computer using specially derived algorithms for enhancing the detection of contamination.

The theoretical development of algorithms which are used for this purpose is based on the difference between spectral reflectance of contaminants versus that of uncontaminated food. The assumption is made that a mathematical combination of remotely sensed spectral bands could be used to identify contaminants. The results generated by such a combination of spectral bands corresponds to the amount of contaminants in a given image pixel.

There are two categories of algorithms that have been developed for use in the detection of contaminants. The first is a ratio of key wavelengths or bands that are determined. The purpose behind using a ratio is to alter the reflectance measurements of spectral bands using an illumination independent function, which will augment the spectral values for the contaminant while diminishing the values for the food source or background.

Examples range from a simple ratio of two wavelength images, to a ratio of multiple wavelength image combinations, such as $$\left( \frac{(\lambda_1 + x)^2 (\lambda_2 - \lambda_4)}{(\lambda_1 + \lambda_3)(\lambda_2)} \right)$$

where $\lambda_1, \lambda_2, \lambda_3,$ and $\lambda_4$ are images at four key wavelengths, and x is a constant. Another example in the ratio category would be the well-known normalized difference vegetative index (NDVI).

The second category of algorithm is defined as a linear combinations of wavelengths. The linear combinations category can range from a combination of two wavelengths $(\lambda_1 + \lambda_2)$, to a linear combination of wavelength ratios, such as:

$$\left( \frac{\lambda_1 + \lambda_2 - w}{\lambda_2 - x} \right) + \left( \frac{\lambda_1 + \lambda_3 - w}{\lambda_3 - x} \right) - \left( \frac{\lambda_1 + \lambda_4 - y}{\lambda_4 - z} \right)$$

where $\lambda_1, \lambda_2, \lambda_3,$ and $\lambda_4$ are images at four key wavelengths, and w, x, y, and z are constants. This category also includes previously published remote sensing algorithms such as the Mahalonobis Distance and the rule file generation of the Spectral Angle Mapper. These formulas may need to be combined with a known filter for optimum results. Once an equation has been used, it may be necessary to apply any of a number of imaging filters to the resultant data set, either for clarity, to sharpen results, or even to limit the error. Some examples of these are low pass, high pass, median, gaussian, laplacian and texture filters.

Further objects and advantages of the invention will become apparent from the following description.

BRIEF DESCRIPTION OF THE DRAWINGS

The claim of this patent contains at least one drawing executed in color.

FIGS. 1a (Front view), 1b (Side View), and 1c (camera assembly) show a schematic of an imaging system 10 including a means for obtaining spectral images 12-SensiCam camera containing at least one charge-coupled device detector 1A with spectrograph 1C, and lens assembly 1B; two quartz-halogen line lights 2B; fiber-optic cables 2A, power supply 2C for lighting; power supply 4 for detector 1A; battery backup 5; computer monitor 6, computer 7, and interface cable 7A.

FIGS. 4a and 4b illustrate a digital filtering technique common to two embodiments of the present invention.

FIG. 11a is a 517-nm image divided by 434-nm image. FIG. 11b is a 565-nm image divided by 434-nm image. FIG. 11c is a 628-nm image divided by 434-nm image; figure d is a 565-nm image divided by 517-nm image. FIG. 11e is a 628-nm image divided by 517-nm image. FIG. 11f is a 628-nm image divided by 565-nm image.

FIG. 13a shows an unmasked image (565-nm image divided 517-nm image).

FIG. 14a shows a ratio image, after the masking procedure, with contaminants somewhat visible in white. FIG. 14b shows a ratio image, after the histogram stretching procedure, with contaminants clearly visible in white. #14b.1-contaminant below the tail, #14b.2-row of duodenum, #14b.3-row of ceca, #14b.4-row of colon contaminant, and #14b.5-row of ingesta contaminants.

DETAILED DESCRIPTION OF THE INVENTION

Figure 1D:
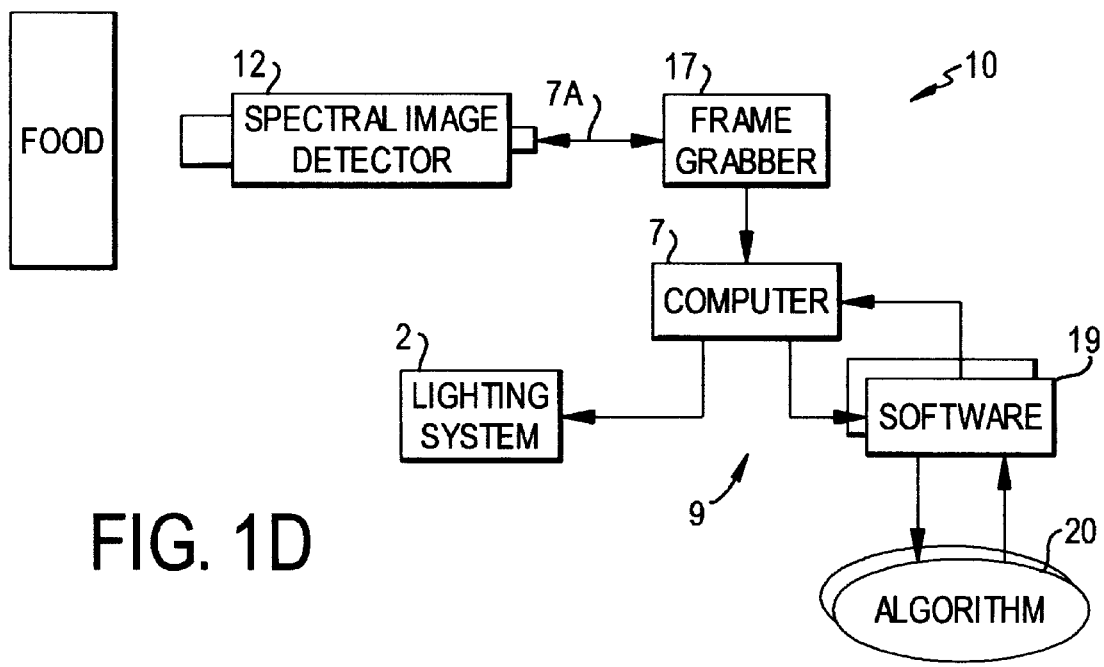
FIG. 1d is a schematic diagram which shows the components of a multispectral contaminant detection system according to one embodiment of the present invention.

Hyperspectral and multispectral imaging are imaging techniques that combine aspects of conventional imaging with spectrometry and radiometry. These techniques are capable of providing an absolute radiometric measurement over a contiguous spectral range for each and every pixel of an image. Data from an image contain two-dimensional spatial information as well as spectral information at each location in the spatial domain. These data can be considered as a three-dimensional hypercube (or data cube) which can provide physical and/or chemical information of a material under test. This information can include physical and geometric observations of size, orientation, shape, color, and texture, as well as chemical/molecular information such as water, fat, and protein.

Generally, for detecting contamination on food, such as for example animal carcasses, testing is conducted at one or more stations along the processing line, during transport along the line, or soon after completion of slaughter. For the purposes of this application, contamination of animal carcasses is to include but not be limited to, digestive tract material including fecal contamination, ingesta contamination, crop contents, bacterial contamination, etc. At the testing stations, the carcasses may be imaged with a hyperspectral or multispectral imaging system at any contiguous or discrete wavelengths of radiation from about 400 to about 2500 nm emitted therefrom and detected as described herein below. Because processing facility practices vary with the particular meat producing animal, specific locations for testing along the processing line will vary. For instance, the typical processing line for poultry include the following steps in order: the bird is suspended by the legs in a shackle, electrically stunned, bled via a neck cut, hard or soft scalded, defeathered, decapitated, and eviscerated (usually by mechanical means), and chilled in chlorinated ice-water baths. On the other hand, beef harvest procedures differ significantly, and include the following steps: the animal is inspected, rendered unconscious, shackled, hoisted, exsanguinated and placed onto a moving rail. The carcass is then skinned (primarily through the use of mechanical hide pullers) and the head is removed for postmortem inspection of wholesomeness. Prior to evisceration, the brisket is split and the esophagus and anus are loosened (these may be tied to prevent fecal and ingesta contamination of the carcass). The abdominal cavity is then opened with a vertical incision through the abdominal muscles and the internal organs (excluding the kidneys) and the entire gastrointestinal tract are removed onto a conveyor for postmortem inspection and further processing. The eviscerated carcass is then split into halves, cutting longitudinally through the spinal column, and inspected for wholesomeness. Once inspection is complete (passed), the carcass sides are mechanically washed (which may include a steam pasteurization step to minimize microbial contamination), weighed, and chilled for 24 to 48 hours before fabrication into primal and subprimal cuts and subsequent shipment. Pork harvest procedures are similar to beef, with the exception where the skinning step in the beef process is replaced by a hair removal process in pork that leaves the skin on the carcass. Scalding the carcass in hot water to loosen the hair follicles, mechanically removing the hair, singeing to remove any residual hair, and subsequently washing and rehanging the carcass accomplish this. Evisceration is similar to beef and pork carcasses are split into sides through the spinal column; however, the skin and soft tissue are left intact at the anterior end of the carcass. Inspection, washing, and chilling procedures are also similar to beef. In some instances, pork carcass may be deboned while warm, ground with other ingredients such as spices, and rapidly chilled to refrigeration temperatures. Testing may be conducted during or upon completion of any of the above-mentioned steps.

In one example, beef or pork carcasses can be inspected for contamination prior to chilling of the sides or carcass usually within approximately 2–3 minutes after splitting or in less than 10 minutes of initiation of harvest, depending on the species. Other sites for inspecting may include after skinning, after evisceration, and(or) after splitting. Poultry carcasses can be inspected for contamination after defeathering and/or evisceration. For quality control, poultry may also be inspected following removal from chilled chlorinated ice-water baths.

Imaging systems 10 (FIG. 1d) include a means for obtaining spectral images 12, a lighting system 2, and data processing unit 9. One embodiment of the present invention includes a hyperspectral imaging system 10 (FIGS. 1a–c). Hyperspectral imaging system 10 includes at least a means for obtaining spectral images 12, such as for example at least one charge-coupled device detector 1A; lighting system 2, and data processing unit 9. The means for collecting spectral images 12 for the purposes of this embodiment, includes at least one charge-coupled device 1A, a lens assembly 1B, and a line-scan spectrograph 1C. It further includes a power supply 4 and a battery back-up 5.

Device 1A can be a high resolution detector, such as for example, a Charge-Coupled Device detector (CCD). Examples of a charge-coupled device detector include, for example, a SensiCam 370 KL Camera (Cooke Cooperation, Auburn Hills, Mich.); an Orca 100 Digital CCD Camera system (Hamamatsu, Bridgewater, N.J.); a SpectraVideo 16-bit Digital (PixelVision, Inc., Beaverton, Oreg.); etc.

Line-scan spectrograph 1C has a nominal spectral range of from about 400 nm to about 900 nm and attaches to the CCD detector 1A for generating line-scan images. Lens assembly 1B includes a 1.4/17-mm compact C-mount lens such as, for example, a Xenoplan (Schneider, Hauppauge, N.Y.); Nikkor (Nikon Inc., Melville, N.Y.); and attaches to spectrograph 1C.

Another embodiment of the present invention includes a multispectral imaging system 10. Multispectral imaging system 10 includes a means for obtaining spectral images 12, a lighting system 2 and a data processing unit 9. In this embodiment, a means for obtaining spectral images 12 for a multispectral imaging system includes a common aperture camera having two or more detectors, such as two CCD detectors, for simultaneously acquiring multispectral images. The camera utilizes a wavelength-separating prism, a dichroic filter, to split broadband light, which enters the camera through the lens, into at least two independent optical channels. The degree of specific spectral separation between optical channels depends upon the dichroic filter and the subsequent trim filter properties. Specifically, the separation is a function of the desired key wavelengths as determined by the calibration model for the specific food and its associated contaminants, their proximity to each other, and the bandwidth of the trim filters. The wavelength separating prisms or filters contain different dichroic coatings on different faces of the prism which determines the performance of the camera. The optical trim filters, between the prism exit plane and the detectors, determine the spectral bandwidth reaching the detectors and are designed such that the central wavelength corresponds to one of the key wavelengths. As a result of this process, two or more spectral images are obtained simultaneously. By way of example, a common aperture camera system with two detectors is described. Common aperture cameras with three or more detectors are also feasible. These cameras would result in simultaneously acquiring three or more spectral images.

It is of course possible to achieve similar means for obtaining spectral images 12 by using multiple digital imaging devices, such as CCD devices, each having its own filter, for isolation of a preselected wavelength band. Another means for obtaining spectral images 12 is at least one charge-coupled device detector containing area scan filters, such as for example, a liquid crystal tunable filter, an acousto-optic tunable filter, etc. The bandwidths for these filters are specified according to the type of data to be collected. The determination of the bandwidths needed is well within the ordinary skill in the art in light of the detailed description of the present application. The at least one charge-coupled device detector with filters has to be capable of collecting at least two discrete spectral images.

The image signals provided by the means for obtaining spectral images 12 are input to a computer 7 via a known frame grabber 17, such as, for example, a 12-Bit PCI interface board (Cooke Company, Auburn Hills, Mich.; National Instruments, Austin, Tex.). The frame grabber 17 assembles the data into respective image frame files. These data are then processed by the computer 7 according to one of the different processes, including differing processing algorithms 20 and method steps, depending on the nature of the production line processing the food. The end result of such computer analysis is the generation of a qualitative analysis such as a "contaminated/uncontaminated" determination for each unit of food that passes in front of the means for obtaining spectral images or a quantitative determination to determine, for example, types and/or size of contamination.

The theoretical development of algorithms 20 which are used for this purpose is based on the difference between spectral reflectance of contaminants versus that of uncontaminated food. The assumption is made that a mathematical combination of remotely sensed spectral bands could be used to identify contaminants. The results generated by such a combination of spectral bands corresponds to the amount of contaminants in a given image pixel.

There are two categories of algorithms that have been developed for use in the detection of contaminants. The first is a ratio of key wavelengths or bands that are determined. The purpose behind using a ratio is to alter the reflectance measurements of spectral bands using an illumination-independent function, which will augment the spectral values for the contaminant while diminishing the values for the food source or background.

Examples range from a simple ratio of two wavelength images, to a more complex ratio such as:

$$\left( \frac{(\lambda_1 + x)^2 (\lambda_2 - \lambda_4)}{(\lambda_1 + \lambda_3)(\lambda_2)} \right)$$

where $\lambda_1$, $\lambda_2$, $\lambda_3$, and $\lambda_4$ are images at four key wavelengths, and x is a constant. Another example in the ratio category would be the well-known normalized difference vegetative index (NDVI).

The second category of algorithm is defined as a linear combination of wavelengths. The linear combination category can range from a combination of two wavelengths, $(\lambda_1 + \lambda_2)$, to a linear combination of wavelength ratios such as:

$$\left( \frac{\lambda_1 + \lambda_2 - w}{\lambda_2 - x} \right) + \left( \frac{\lambda_1 + \lambda_3 - w}{\lambda_3 - x} \right) - \left( \frac{\lambda_1 + \lambda_4 - y}{\lambda_4 - z} \right)$$

where $\lambda_1$, $\lambda_2$, $\lambda_3$, and $\lambda_4$ are images at four key wavelengths, and w, x, y, and z are constants. This category also includes previously published remote sensing algorithms such as the Mahalonobis Distance and the rule file generation of the Spectral Angle Mapper. These formulas may need to be combined with a known filter for optimum results though. Once an equation has been used, it may be necessary to apply any of a number of imaging filters to the resultant data set, either for clarity, to sharpen results, or even to limit the error. Some examples of these are low pass, high pass, median, gaussian, laplacian and texture filters.

Both the hyperspectral and the multispectral systems require lighting system 2. Lighting system 2 includes an illuminator with at least 2400 lux (lumen/m$^2$) intensity and excitation wavelengths between about 400 and about 2500 nm, such as for example, Fiber-Lite A240 (Dolan-Jenner, Inc., Lawrence, Mass.); lamp assembly 2B, for example quartz halogen line lights such as for example QF5048 (Dolan-Jenner, Inc.); lighting power supply 2C, and fiber-optic cables 2A.

Figure 2:
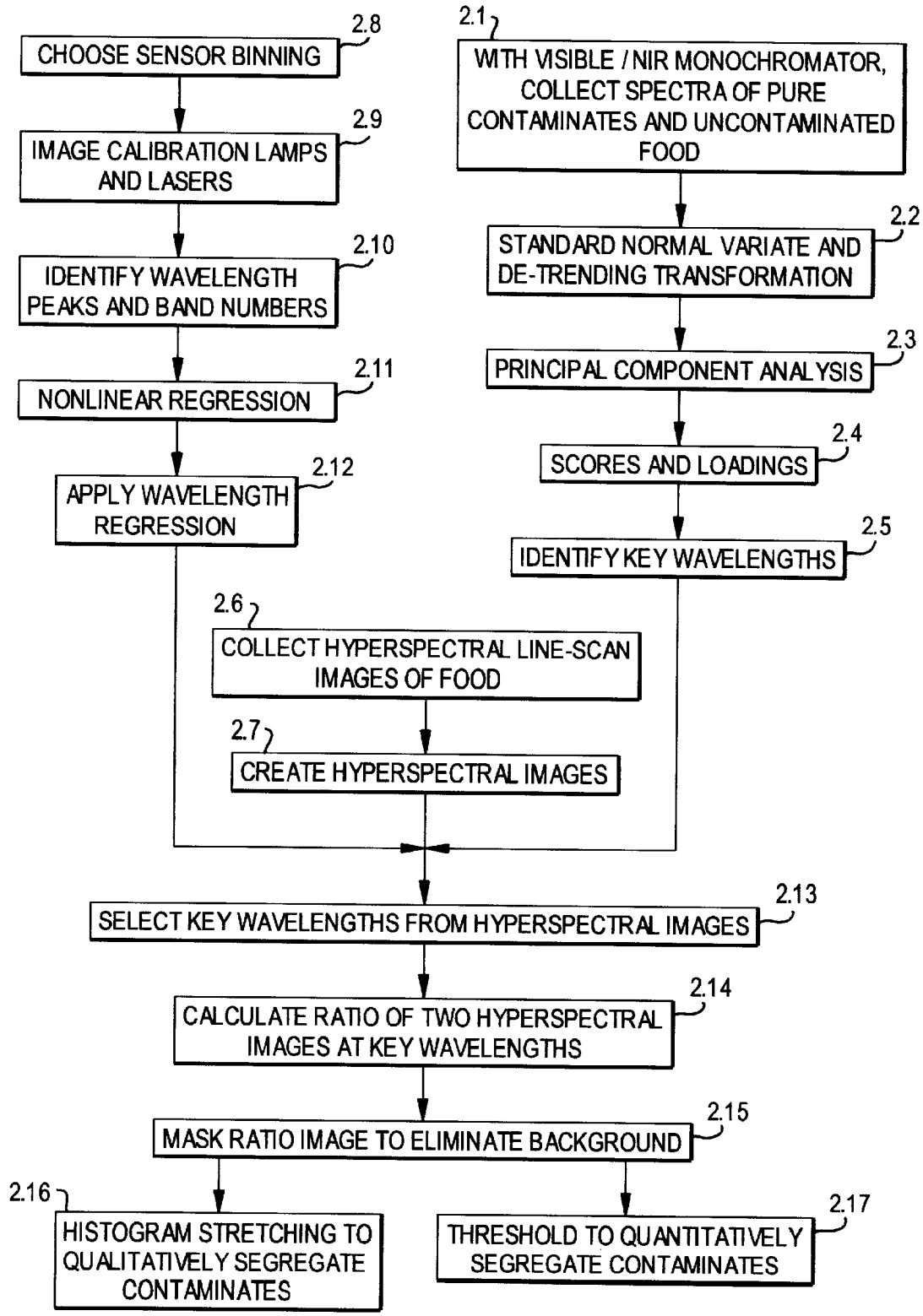
FIG. 2 is a flowchart for the detection of contaminants on food such as feces and ingesta on the poultry carcasses with Vis/NIR monochromator (2.1–2.5) and hyperspectral imaging system 10 (2.6–2.17).

Data analysis (Microfiche Appendix) is needed in order to determine particular types of contamination on foodstuffs. A calibration model correlates band numbers of the imaging system with actual wavelengths. Referring to FIG. 2, the first step is to collect spectra of pure contaminants and uncontaminated food with a Vis/NIR monochromator, for example, a NIRSystems 6500 monochromator (NIRSystems, Silver Spring, Md.) which has a spectral range from about 400 to about 2500 nm in about 2-nm intervals (FIG. 2, Box 2.1). Before each sample is measured, a standard ceramic tile, having high reflectance, is measured to provide standard reflectance values. The reflectance values of the samples and the standard are converted to log (1/R) values where R is reflectance. It is known to convert reflectance data representing log (1/R) values, wherein R is reflectance, which values vary approximately linearly with the concentration of the absorber. Generally, any suitable monochromator may be utilized, provided that the resulting spectra covers both visible and NIR regions. This means that the wavelength of visible light will be in the range of about 400 to about 780 nm, and NIR light will be in the range of about 782 to about 2500 nm.

After the data are converted to log (1/R), the next step is to transform the converted data with standard normal variate and detrending or multiplicative scatter correction to remove interferences of scatter, particle size, variation in baseline shift, and curvilinearity (FIG. 2, Box 2.2). Variation within individual Vis/NIR spectra is the result of three main sources: 1) nonspecific scatter of radiation at the surface of the sample; 2) variable spectral pathlength through the sample; and 3) chemical composition of the sample. Scatter is dependent on the physical nature of the sample particles and pathlength is largely dependent on sample particle size. There is a high degree of collinearity between data points in the log (1/R) spectra, which is a function of scatter and variable pathlength. The multiplicative combinations of these effects are unique to any one spectrum, and any corrections for these interference should be made on the same basis. These interferences can cause problems in quantitative and qualitative analysis and should be removed prior to calibration and analysis. Spectral measurements of pure contaminants and uncontaminated foodstuffs are transformed with standard normal variate and detrending procedures (Barnes et al., Appl. Spectrosc., Volume 43 (5), 772–777, 1989; herein incorporated by reference) to remove interferences of scatter and particle size, and variations in baseline shift and curvilinearity. The invention is not limited to any one specific mathematical transformation to remove these interferences. It has been found that NIR ratio techniques (Norris, Karl, U.S. Pat. No. 5,132,538; herein incorporated by reference), second derivative transformation, and multiplicative scatter correction (Geladi et al., Applied Spectrosc., Vol. 39(3), 491–500, 1985; herein incorporated by reference) show sufficiently similar corrections within the scope of the present invention.

After transforming the log (1/R) data, as described above, the transformed data is processed with Principal Component Analysis (PCA) for formation of scores and loadings (FIG. 2, Box 2.3). Examples of commercially available software for performing PCA analysis include Winisi, Infrasoft, Port Matilde, Pa.; Unscrambler, CAMO, Oslo, Norway; Grams/32, Galactic Industries Corp., Salem, N.H.; etc. Mathematical tools have been developed to help extract additional information from spectra. Chemometrics have been described as the application of mathematical and statistical methods to extract more useful information from chemical and physical measurements. Recent advances have lead to new data analysis systems and commercially available Vis/NIR instruments that use one or more chemometric methods for qualitative and quantitative analysis. Standard practices for chemometrics in infrared, multivariate, qualitative, and quantitative analysis are described elsewhere (American Society for Testing Materials (ASTM) Practice, E1655–94, 1995; ASTM Annual Book of Standards, West Conshohocken, Pa., Volume 3.06, 1995; both herein incorporated by reference). Principal Component Analysis (PCA) is one technique for identifying the underlying features of large data sets, and attempts to describe the variation in multi-dimensional data by means of a small number of uncorrelated variables. The underlying concepts and properties of PCA are described in Barton et al., (U.S. Pat. No. 6,114,699; herein incorporated by reference). Briefly, PCA is a variable reduction procedure. It is useful on a large data set with a large number of variables that are correlated to each other. Because of these intercorrelations, the observed variables can be reduced into a smaller number of artificial variables (principal components, eigenvectors, factors, or T-variables) that will account for most of the variance in the observed variables. Translated into principal components, the new coordinate system has fewer dimensions than the original set of variables, and the directions of the principal components describe the largest variations. The localization, or the coordinates of the samples related to the principal components, are called scores (Eigenvalues). The corresponding relationship between the original variables and the new principal components are called loadings (weights). The next step is to compare scores with variations in principal components to select discrete principal components at which scores correlate with uncontaminated foods and contaminants (FIG. 2, Box 2.4). The spectra of samples are analyzed by principal component analysis as described above, and scores and loadings are used to select key Vis/NIR wavelengths for discrimination between contaminated and uncontaminated foods. It has been found that partial least squares regression (Workman et al., Applied Spectrosc. Reviews, Volume 31(1&2), 73–124, 1996; herein incorporated by reference) can also be used for modeling the variance within spectra of pure contaminants and uncontaminated foods to identify key wavelengths (FIG. 2, Box 2.5). Once key wavelengths are identified for a particular food and its associated contaminants, these can be used in any embodiment of the present invention.

After key wavelengths are identified from the calibration model generated for a particular food and its associated contaminants, the systems of the present invention are ready to image foods for contamination. For hyperspectral imaging system 10, line scan images are collected (FIG. 2, Box 2.6). With hyperspectral imaging, all spectral wavelengths can be collected for every pixel of an object. Data are acquired with a high resolution CCD image detector, which is a two-dimensional focal-plane array sensor. Therefore, only two dimensions of an image can be collected at any given time. A typical embodiment is a single line-scan image which consists of spectral information for one spatial row. Line-scan images are taken while the food source is moving so that the successive line scans represent successive slices of the food source. Alternatively, the food source may remain stationary and the camera may move. Successive line-scan images are collected by computer 7 via a frame-grabber 17 that interfaces the CCD detector through interface cable 7A. Once the frame-grabber has stored line-scan images as data files in computer 7, they may be combined to create a full hyperspectral image that has two-dimensional spatial information as well as spectral information (FIG. 2, Box 2.7). This full hyperspectral image is sometimes referred to as a three-dimensional hypercube. The hyperspectral image is created through software which combines the individual line-scan image files into a single hyperspectral image file such as for example Hypervisual (Provision Technologies, Stennis Space Center, Miss.); Interactive Data Language (IDL)(Research Systems, Inc., Boulder, Colo.), etc. However, any software capable of creating a hyperspectral image is useful in the present system and is well within the ordinary skill in the art given the detailed description of the present invention.

The next step in the process is to choose sensor binning (FIG. 2, Box 2.8). The choice of hyperspectral imaging resolution is determined by the food source imaged, the minimum physical size of the contaminant, and the values of the key wavelengths determined from the Vis/NIR monochromator. The imaging resolution is a function of both the CCD detector dimensions and the binning selected during image capture. Binning describes the process where photons collected in adjacent pixels are summed together. For example, a binning of 4 by 2 applied to a CCD with 1280 by 1024 pixels would result in the summing of photons collected over eight adjacent pixels (two rows of four columns). The result would be line-scan images with an image resolution of 320 pixels (1280 divided by 4) in the spatial dimension and 512 pixels (1024 divided by 2) in the spectral dimension. The spectral dimension is sometimes referred to as the bands.

The hyperspectral imaging system requires a wavelength calibration so that the intensities at various band numbers will correspond to an actual wavelength. Thus, after wavelength calibration, the same key wavelengths, identified with the Vis/NIR monochromator (FIG. 2, Box 2.5 and described above), can be evaluated with the hyperspectral imaging system. The hyperspectral wavelength calibration equation was developed from separate hyperspectral image data (FIG. 2, Box 2.9) of spectral calibration lamps (Oriel Instruments, Stratford, Conn.) and lasers (Edmund Scientific, Barrington, N.J.) inserted into an integrating sphere (Optronic Laboratories, Inc., Orlando, Fla.; Labsphere, North Sutton, N.H.). The integrating sphere disperses the energy from the calibration lamps so that any image system looking into the integrating sphere observes a spatially uniform image. The calibration lamps must have precise distinct wavelength peaks across the wavelength range of the hyperspectral imaging system needing calibration. Determination of these is well within the ordinary skill in the art.

After imaging the spectral calibration sources, distinct wavelength peaks and their corresponding band numbers are identified (FIG. 2, Box 2.10) and for a given binning, regressed (FIG. 2, Box 2.11) against the corresponding image band numbers as follows:

$$\text{wavelength (nm)} = 380.277 + 0.905 + (4.369 \times 10^{-4})X^2 - (4.356 \times 10^{-7})X^3 \, (r^2=0.9999)$$

where X is the band number ranging from about 0 to about 511 (FIG. 2, Box 2.11). This wavelength calibration equation is independent of light intensity but is dependent on the individual CCD detector and will have different coefficients for different detectors and binning combinations. The wavelength calibration is then applied to all subsequent images of food (FIG. 2, Box 2.12). Given this detailed description of the present invention, it is well within the ordinary skill in the art to develop a calibration equation for a given sensor.

The next step is to select hyperspectral images (FIG. 2, Box 2.13) with the key wavelengths identified earlier (FIG. 2, Box 2.5). Then a ratio image is calculated where, in the simple case, the intensity of one image is divided by the intensity of a corresponding image at a different key wavelength on a pixel-by-pixel level (FIG. 2, Box 2.14). This allows for the generation of ratio images that are used to identify and locate contamination on the food source.

To further enhance an image, the image background is eliminated through a masking procedure (FIG. 2, Box 2.15). Histogram stretching is used to visually enhance the contaminants (FIG. 2, Box 2.16). Masking is a process where all pixel intensities below a minimum value are assigned to a fixed value (zero). Since the calculated ratio-image values vary (FIG. 2, Box 2.14) from about 0 to about 2, masking is performed on one of the original key wavelength images and then transferred to the ratio image by assigning all corresponding ratio image intensity values to zero. For example, the image at 565-nm has an intensity value of less than about 120 for the background. Thus, any pixels below the minimum value of 120 in the 565-nm image are assigned a value of zero in the ratio image, which removes the background.

Histogram stretching is a method to enhance the contrast of a displayed image. Typically, it is a linear stretching of the image intensity values to the full-scale display range (0 to 255 gray-scale) where the minimum image intensity value is assigned to a full-scale display value (255 for 8-bit grayscale). However, for the masked ratio images, a histogram stretch is applied such that all image intensity values below a low threshold value are assigned a zero display value, and all those above a high threshold value are assigned a full display-scale value, with intermediate values assigned linearly proportional display values between the zero and full display-scale values. The method to this point would be suitable as a decision tool for food inspectors in the identification of the presence of contaminants.

Another alternative to histogram stretching is to use a threshold routine to quantitatively identify contaminants (FIG. 2, Box 2.17). The threshold routine changes all pixel intensity values below a given contaminant threshold value to zero. The contaminant threshold is chosen so that all pixels greater than the threshold value are identified as contaminants. This is applicable for real-time identification of food contamination in a processing line.

For the multispectral imaging system 10 embodiment, spectral images at least two wavelengths are collected (FIG. 3, Box 3.1) with a means for collecting spectral images 12 as described above. The spectral data is then analyzed using a software program 19 containing the necessary algorithms 20 and process steps. A software program 19 is stored in the memory of a computer 7 (FIGS. 1a–d).

Figure 3:
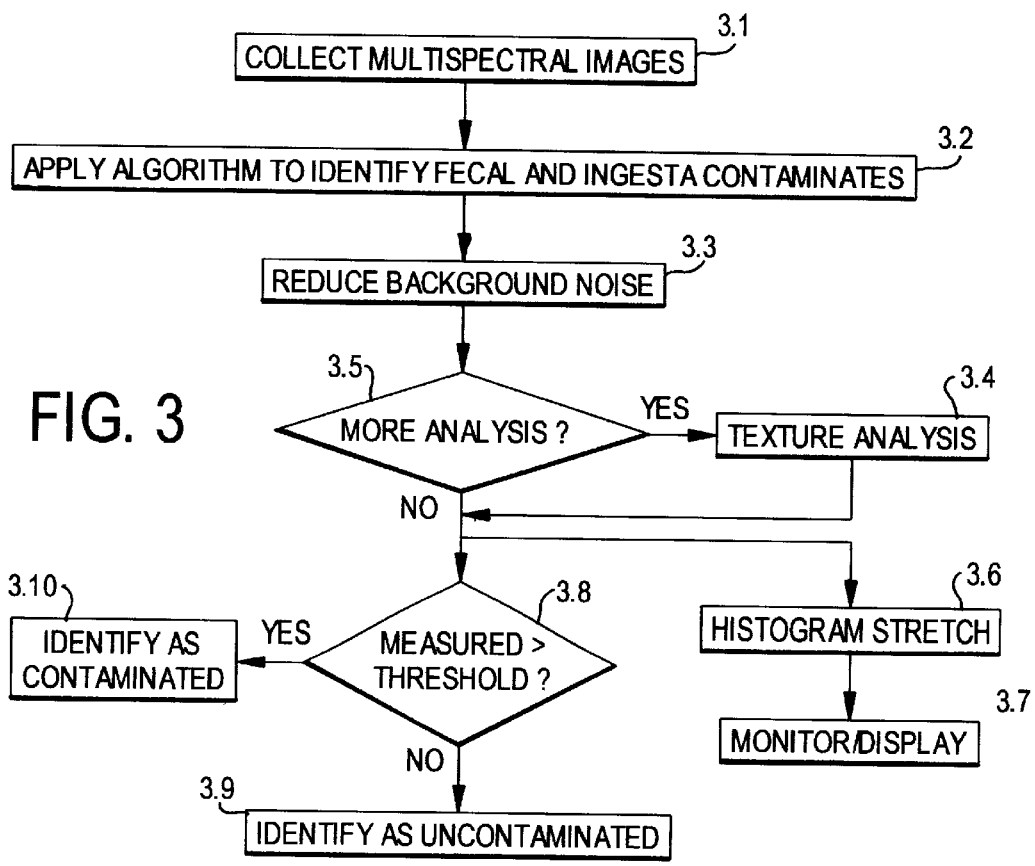
FIG. 3 is a flowchart for the detection of contaminants on food such as feces and ingesta on poultry carcasses with a multispectral imaging system where key wavelengths have already been determined.

One example of an algorithm 20 for a first step in analyzing the spectral data is to calculate a ratio image at two key wavelengths to detect contaminants (FIG. 3, Box 3.2). Multispectral wavelengths are first collected (FIG. 3, Box 3.1) at the key wavelengths as discussed above for the hyperspectral imaging embodiment. Then the image at one key wavelength is divided by the image at another key wavelength. When this type of calculation is used the next step, is to reduce the background noise by separating the contaminated foodstuff from its background with a masking procedure (FIG. 3, Box 3.3) as discussed above for the hyperspectral imaging embodiment. The fourth step, for this embodiment, separates the contaminants from the foodstuff with histogram stretching (FIG. 3, Box 3.6) for display or monitoring purposes (FIG. 3, Box 3.7) for qualitative separation, while the fifth step, for this embodiment, is a threshold procedure which quantitatively separates the contaminants from the foodstuff (FIG. 3, Box 3.8), as described for the hyperspectral imaging embodiment.

Another embodiment for analyzing spectral data is illustrated in FIG. 3 with a system as depicted in FIG. 1d which is used to detect contamination on poultry carcasses which have been hard scalded prior to removal of feathers. The carcass is illuminated by a light source 2 which provides a predetermined spectral profile. In this case, it has been determined that a light source corrected to about 5600K is particularly advantageous.

Data representing a multispectral image of light reflected from the target carcass are generated by the spectral image detector 12 in four wavelengths (FIG. 3, Box 3.1). In particular, it has been determined that the following four ranges of wavelengths are particularly advantageous for this purpose:

$\lambda_1$=about 750–830 nm $\lambda_2$=about 450–500 nm $\lambda_3$=about 500–535 nm $\lambda_4$=about 550–585 nm The image data generated (FIG. 3, Box 3.1) thus provide four reflectance values, each represented by a digital number (DN), for each pixel included in the acquired image—one such digital number for each of the frequency bands $\lambda_1$–$\lambda_4$. These values are combined to generate a value I for each pixel (FIG. 3, Box 3.2), according to the following algorithm:

$$I = \frac{(\lambda_1 - n)(\lambda_3 + \lambda_4)}{\lambda_3(\lambda_1 + \lambda_2)}$$

wherein n is an integer constant. Subtraction of the constant n in the numerator as indicated in Equation 1, reduces the amount of background noise (FIG. 3, Box 3.3) by altering the DN values of the specified wavelength $\lambda_1$. The result of the above calculation, which is performed in computer 7 of FIG. 1d is the creation of an image file having a single DN value for each pixel.

The DN values generated are then filtered by a process referred to as "texture analysis" (FIG. 3, Box 3.4), which characterizes the image according to real variations in pixel brightness—that is, DN values—to generate two new output image files indicative of the mean and variance for pixels within a moving window of about a 3 by 3 pixel mask, as illustrated in FIGS. 4a and 4b.

FIG. 4a shows the manner of calculation of mean values in the texture analysis. For each window of nine pixels (about a 3 by 3 pixel set) a mean value of the DN values is determined.

For example, in FIG. 4a, three windows a, b, and c are indicated by brackets, with window a being enclosed by a heavy line. The mean of DN values in window a is about 4.2. Similarly, the mean value for window b, enclosed by a dashed line, is about 3.2, as also shown in the set of mean values. As the window is moved over the whole of the image file, a complete new image file of mean values is created. It is of course apparent that different sizes and shapes of windows can be used for this purpose.

The technique of calculation of a new image data set of variance values, shown in FIG. 4b, is similar to that used to calculate the mean values in FIG. 4a.

As is apparent, the performance of the texture analysis (FIG. 3, Box 3.4) yields two image data sets, representing the spatially distributed mean and variance values, respectively for the data values I (FIG. 3, Box 3.2). The mean and variance values are then added together to form a final output image.

Finally the output image is analyzed by computer 7 to determine whether ingesta or fecal contamination is present on the imaged carcass. This can be done, for example, by establishing a threshold value, IF which is indicative of contamination. In this case, calculated values in the final output image data are compared with a threshold value and a decision is made based on such comparison. For example, a positive contamination judgement (FIG. 3, Box 3.10) could be made if a single pixel value exceeds the threshold value, or a judgement of contamination could be made if a specified minimum number of values exceed the threshold; or a minimum number within a defined proximity. In a preferred embodiment, such a determination is made if the carcass has at least one pixel that exceeds the threshold (FIG. 3, Box 3.10); otherwise, the carcass is concluded to be contaminant free (FIG. 3, Box 3.9).

In another embodiment, for carcasses that are soft scalded, carcasses are illuminated by a 5600K color corrected light source 2 in the same manner as indicated in FIG. 1d. In this embodiment, however, three multispectral image-data sets are acquired by spectral image detector 12 at the following key wavelengths, one image dataset per wavelength range:

$\lambda_1$=about 497–537 nm $\lambda_2$=about 545–585 nm $\lambda_3$=about 608–648 nm That is, DN reflectance values are determined for every pixel at each of the three wavelength ranges $\lambda_1$–$\lambda_3$. Thus, each pixel is characterized by a spectral pattern or "signature" consisting of these three DN values—one for each wavelength range.

Next, an algorithm referred to as Spectral Angle Mapper is applied (FIG. 3, Box 3.2), correlating each of the acquired image-data sets $\lambda$ with predetermined spectral signature values at the detected wavelength ranges $\lambda_1$, $\lambda_2$, and $\lambda_3$, for each of four types of ingesta/fecal contaminants, which differ only in their source within the digestive tract of the carcass prior to dressing; that is in particular, the stomach, the duodenum, the colon, and the ceca. The reflectance values for each of these types of contaminant at the key wavelength ranges varies in a characteristic fashion, and accordingly this characteristic pattern can be used to detect its presence. It is of course apparent that the greater the number of wavelength bands which is used to characterize both the target carcass and the types of contamination, the greater the precision of the correlation. However, it has been determined that the three wavelength range values indicated above are sufficient in practice.

In this embodiment, the Spectral Angle Mapper (SAM) algorithm is calculated (FIG. 3, Box 3.2). The Spectral Angle Mapper is a mathematical function which can be used to determine the degree of spectral similarity between the spectral values for each pixel in the acquired image data set and the corresponding spectral signature values for the four contaminants noted above. The formula for calculation of SAM is as follows:

$$\alpha = \cos^{-1}\left(\frac{\sum_{i=1}^{nb} t_i r_i}{\left(\sum_{i=1}^{nb} t_i^2\right)^{1/2} \left(\sum_{i=1}^{nb} r_i^2\right)^{1/2}}\right) \quad \text{(Eq. 4)}$$

wherein:

$t_i$=detected reflectance value of the target carcass in the $i^{th}$ band, $r_i$ reflectance value of the predetermined spectral signature of a subject contaminant in the $i^{th}$ band; and nb=number of bands i in the image.

In this case, since four different types of contaminants are to be detected, four values of α are calculated for each pixel—one for each of the respective reference spectra—resulting in four image data sets, referred to as Rule Files. By virtue of the SAM algorithm, the data in each of these Rule Files are indicative of the likelihood of contamination of the imaged carcass.

Next, the sum or product of all the Rule Files produces a new image file (FIG. 3, Box 3.2). Thereafter, processing for soft scald carcasses in FIG. 3 proceeds in the same manner as for hard scald carcasses as in FIG. 3. That is, a texture analysis is performed (FIG. 3, Box 3.4); the mean and variance values are combined; and contamination is determined based on the combined image data set (FIG. 3, Box 3.8–3.10).

The following examples are intended only to further illustrate the invention and are not intended to limit the scope of the invention which is defined by the claims. Poultry carcasses are used as a model system for testing the system of the present invention.

EXAMPLE 1

Live birds were obtained from a local broiler house, transported to the grow-out facilities at USDA-Agricultural Research Service in Athens, Ga. and held for about 4 days. The feeding regime was scheduled for meal feeding to provide a consistent amount of fecal material in the digestive tract among birds. Birds were stunned (12 VAC), bled for about 90 seconds, scalded at about 57.5° C. for approximately 2 minutes (e.g. hard scald), or about 53° C. for 50 seconds (e.g. soft scald), and picked. Hard scalding removes the skin cuticle resulting in a white carcass, whereas soft scalding leaves the cuticle intact resulting in a yellow carcass. In order to collect feces and ingesta, four replicates of 20 birds were processed and eviscerated to obtain fecal material from the duodenum, ceca, and colon portions of the viscera, and ingesta from the proventriculus and gizzard. Samples of skin were also taken from the breast. See Table 1 below for control variables and fixed values for digestive tract contents.

TABLE 1

Control Variables and Corresponding Fixed Values

| CONTROL VARIABLES | VALUES |
| --- | --- |
| Bird | 6 week male |
| Diet | Corn/Soybean meal |
| Feed Withdrawal | 8 hours |
| Water Withdrawal | 4 hours |

EXAMPLE 2

Figure 5:
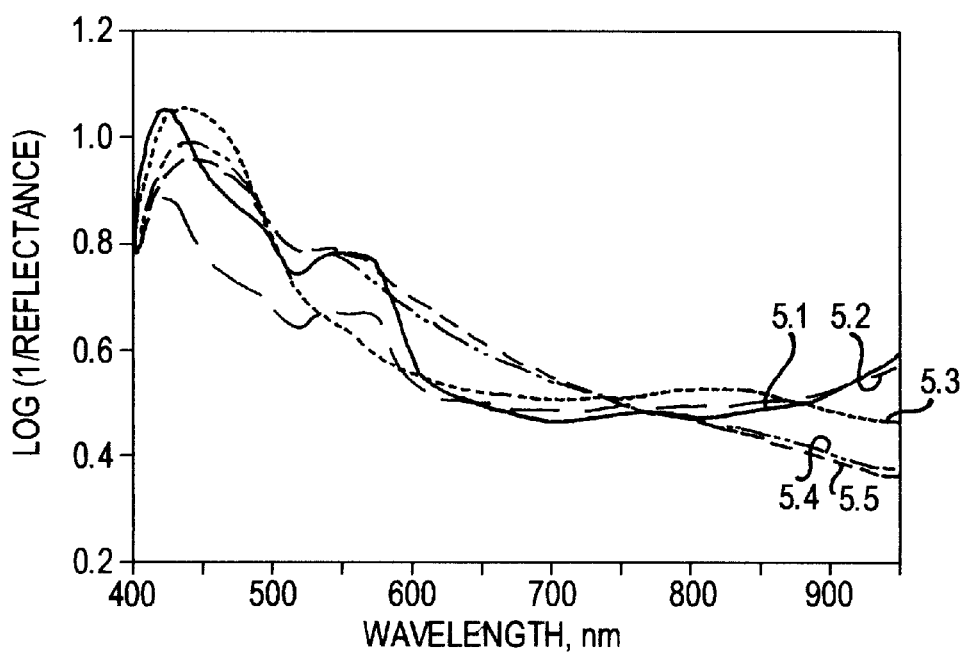
FIG. 5 is a graph showing Vis/NIR reflectance average spectra from a scanning Vis/NIR monochromator of uncontaminated hard (#5.1) and soft (#5.2) scalded poultry carcass skin and pure feces from duodenum (#5.3), ceca (#5.4), and colon (#5.5) samples of poultry viscera.

In order to collect Vis/NIR spectra from carcasses, pure feces from duodenum, ceca, colon and both hard and soft scalded uncontaminated skin were scanned with an NIR-Systems 6500 monochromator (McGee, U.S. Pat. No. 4,969,739, herein incorporated by reference). Spectra were recorded from about 400 nm to about 2500 nm in about 2-nm intervals and analyzed from about 400 nm to about 900 nm. Samples of uncontaminated breast skin were presented in cylindrical sample cells (internal diameter-about 38 mm; depth-about 9 mm) with an optical quartz surface and a cardboard backing. Samples of pure feces were presented in cylindrical sample cells (internal diameter-about 38 mm; depth-about 0.1, 0.2, or 0.3 mm) with an optical quartz surface and a locking back. Each sample was scanned about 32 times, averaged and transformed to log $(1/R_1)$, where R is reflectance. FIG. 5 is the reflectance spectra of uncontaminated poultry carcass breast skin (hard and soft scalded), and pure feces from different sites in the digestive tract. Samples 5.1 and 5.2 are uncontaminated breast skin subjected to hard and soft scald treatments, respectively. Samples 5.3–5.5 are pure feces from the duodenum (5.3), colon (5.4), and ceca (5.5).

A commercial spectral analysis program (NIRS3, Infrasoft International, Inc., Port Matilda, Pa.) was used to collect the spectra of pure contaminates and uncontaminated poultry carcass skin and for principal component analysis (PCA). The spectral data set (n=76 uncontaminated hard and soft scalded skin; N=42 duodenum; N=37 ceca; and N=25 colon) was transformed with standard normal variate and de-trending procedures to remove the interference of light scatter from the skin and differences in pathlength due to sample thickness. The spectra were mean centered and reduced by PCA. Translated into principal components, the new coordinate system has fewer dimensions than the original Vis/NIR data set, and the directions of the new coordinate axes (called principal components) were chosen to describe the largest variations.

Figure 6:
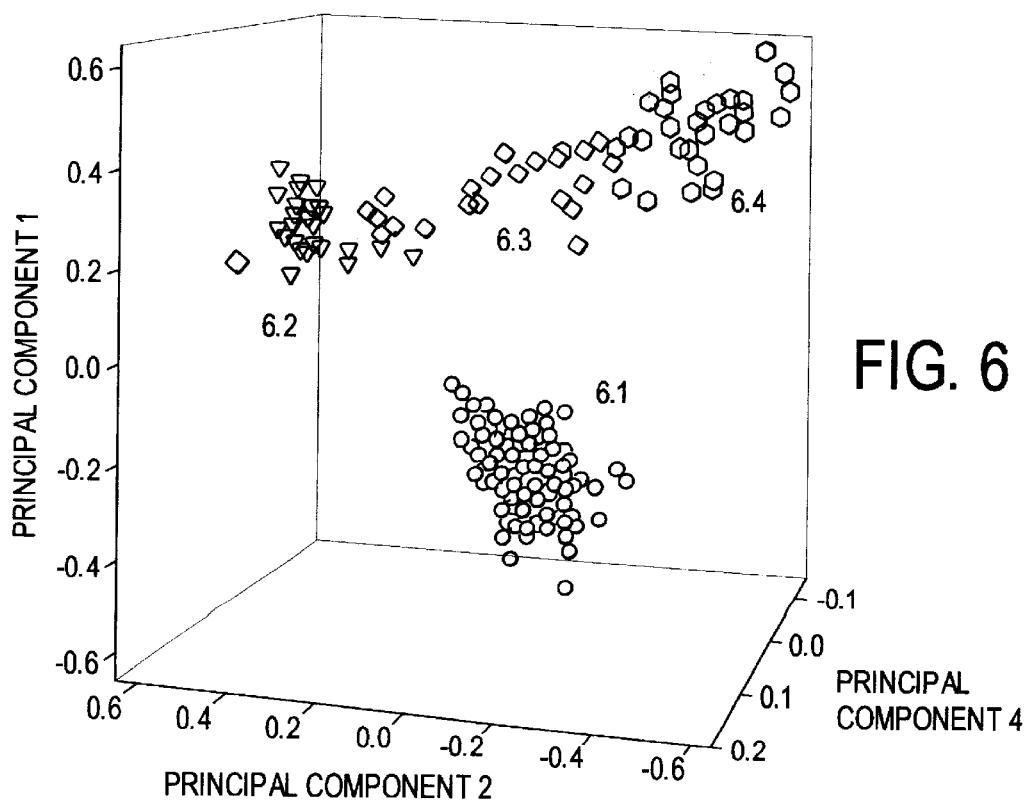
FIG. 6 is a graph showing discrimination of uncontaminated hard and soft scalded poultry carcass skin (#6.1) from duodenum (#6.2), ceca (#6.3 ), and colon (#6.4) feces by Principal Component Analysis of Vis/NIR reflectance spectra.

The PCA algorithm creates scores, which represent the position of samples relative to the principal components. For each principal component, scores are derived by taking the sum across the spectrum of weights times the log (1/R) values. The corresponding relationship between the Vis/NIR spectra and the principal components are called loadings. Plots of loadings often resemble the spectra of samples and thus offer scope for interpretation. Four principal components were used in the PCA. The components explained about 99.8% of the Vis/NIR spectral variation. FIG. 6 shows a clear discrimination between uncontaminated skin and feces using principal components 1, 2, and 4. Principal component 1 (PC 1) was primarily responsible for the separation of uncontaminated skin (FIG. 6, 6.1 hard and soft scald), from duodenum (FIG. 6, 6.2), colon (FIG. 6, 6.3), and ceca (FIG. 6, 6.4). Uncontaminated skin had negative scores for PC 1, whereas pure feces had positive scores for PC 1. Loadings are the regression coefficients for each Vis/NIR wavelength for each principal component and indicate which wavelengths are dominantly influencing the discrimination. From PC analysis, four key wavelengths were identified for discrimination of uncontaminated skin from pure feces based on the loadings.

Figure 7:
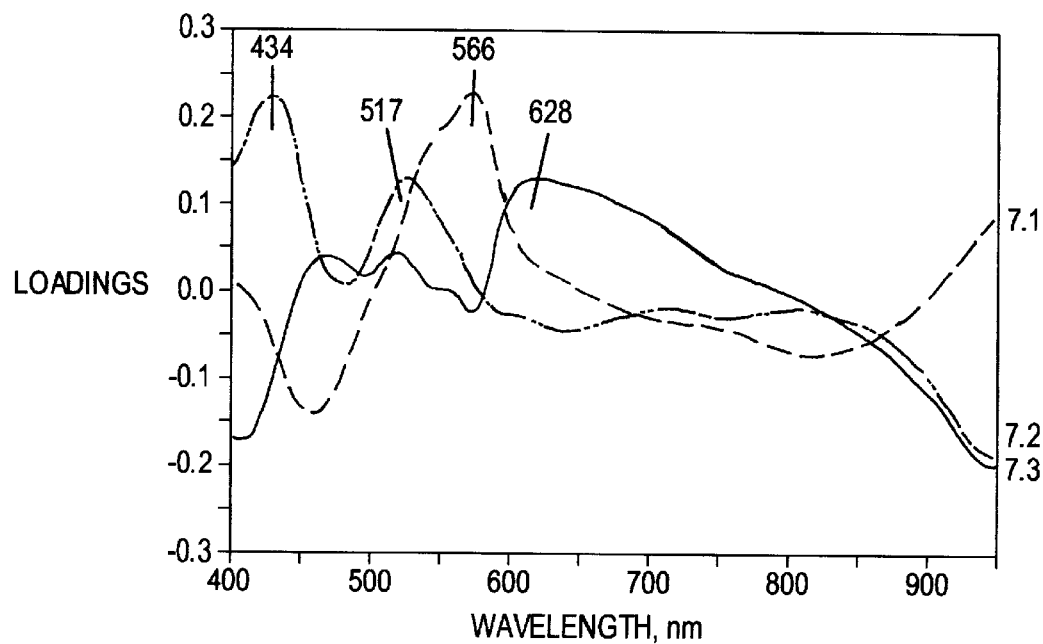
FIG. 7 is a graph showing Principal Component Analysis loadings for Principal Components 1 (#7.1), 2 (#7.2), and 4 (#7.3) as a function of wavelength.

FIG. 7 shows the loadings for PC 1, PC 2, and PC 4 as a function of wavelength. Key wavelengths are identified by maximum loadings at about 565 nm for PC 1 (FIG. 7, 7.1), about 434 and 517 nm for PC 2 (FIG. 7, 7.2), and about 628 nm for PC 4 (FIG. 7, 7.3). These key wavelengths were selected and applied to hyperspectral images of uncontaminated and contaminated carcasses.

EXAMPLE 3

Figure 8:
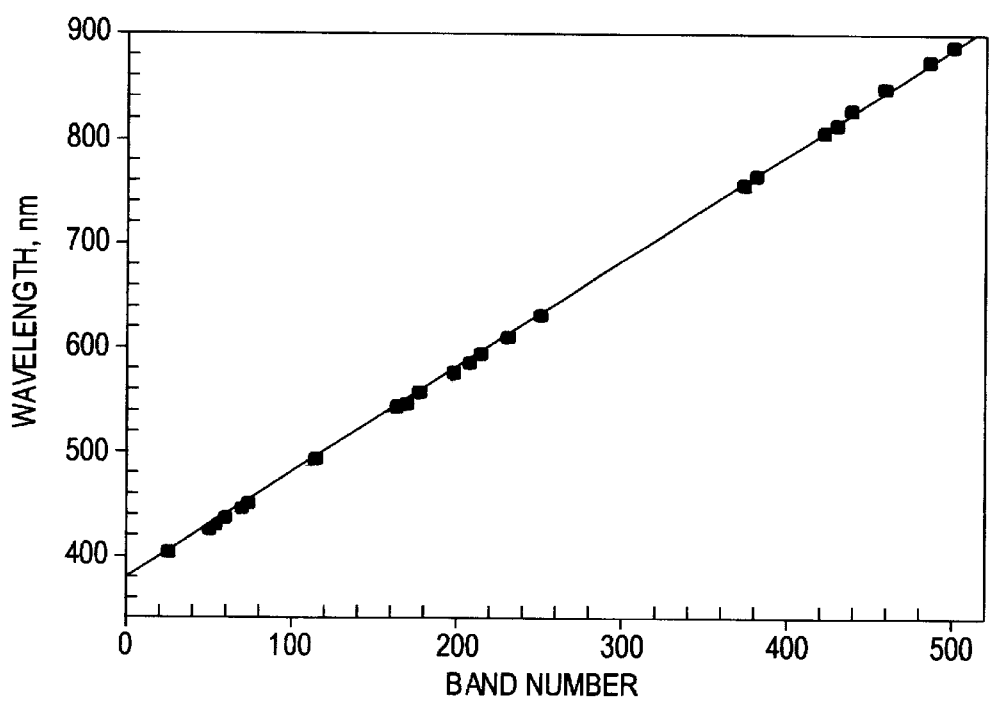
FIG. 8 is a graph showing a non-linear cubic regression model for spectral calibration of the hyperspectral imaging system 10 with a binning of 4 by 2.

Spectral calibration was performed to correlate absolute wavelength data from known spectral light sources of Mercury Argon (HgAr) and Krypton (Kr) gas emission calibration lamps (Model 6035 and 6031, Oriel Instruments, Stratford, Conn., respectively), and Helium-Neon lasers, to the 512-hyperspectral image bands (1024 pixels with a binning of 2) obtained from the CCD detector 1a. FIG. 8 shows the data and the non-linear calibration for the hyperspectral imaging system 10, which was used to correlate the band numbers of the hyperspectral images to the actual wavelengths. The wavelength calibration equation for hyperspectral imaging system 10 is as follows:

Wavelength (nm)=380.277+0.905+(4.369×10$^{-4}$) $X^2$−
(4.356×10$^{-7}$)$X^3$($r^2$=0.9999)

where X is the band number ranging from about 0 to about 511.

EXAMPLE 4

Immediately after processing, as in Example 1, carcasses, fecal, and ingesta samples were used for image acquisition. Carcasses were contaminated with feces from the duodenum, ceca, and colon, and ingesta with varying contaminate size and location. Carcasses were imaged in a shackle welded to a stainless steel rod, suspended across two stands. A laser beam was used to align fiber-optic line-light propagation to make light propagation on the carcasses as diffuse as possible. Light intensity and distribution on the carcasses were measured and optimized with a digital intensity meter (Mavolux 5032C, Gossen, Germany) before image data were collected. Carcasses were imaged with hyperspectral imaging system 10 with 4 by 2 binning and SensiCam™ software with the following control settings: actual image size of about 320 (horizontal) by about 340 (vertical) pixels spatial resolution, and about 512 wavelengths spectral resolution. The spectral resolution of hyperspectral images was approximately 0.9 nm. The exposure time and delay time of camera control during image acquisition were about 50 msec. and zero, respectively. Even though scanning time depends on the size of a carcass and image resolution, the average time to scan a whole carcass was about 34 seconds. Hypercube image files were created from line scan image data with HyperVisual software (ProVision Technologies, Stennis Space Center, Miss.), which converts 16-bit binary data into binary sequence mode data for hyperspectral image processing. First, hyperspectral images of uncontaminated carcasses were collected. Then, carcasses were contaminated with feces and ingesta varying in type of contaminant, contaminant spot size, and location on the carcass. Hyperspectral images and spectral image files were further processed, analyzed, and displayed using Environment for Visualizing Images (ENVI) software (Research Systems, Inc., Boulder, Colo.).

Figure 9:
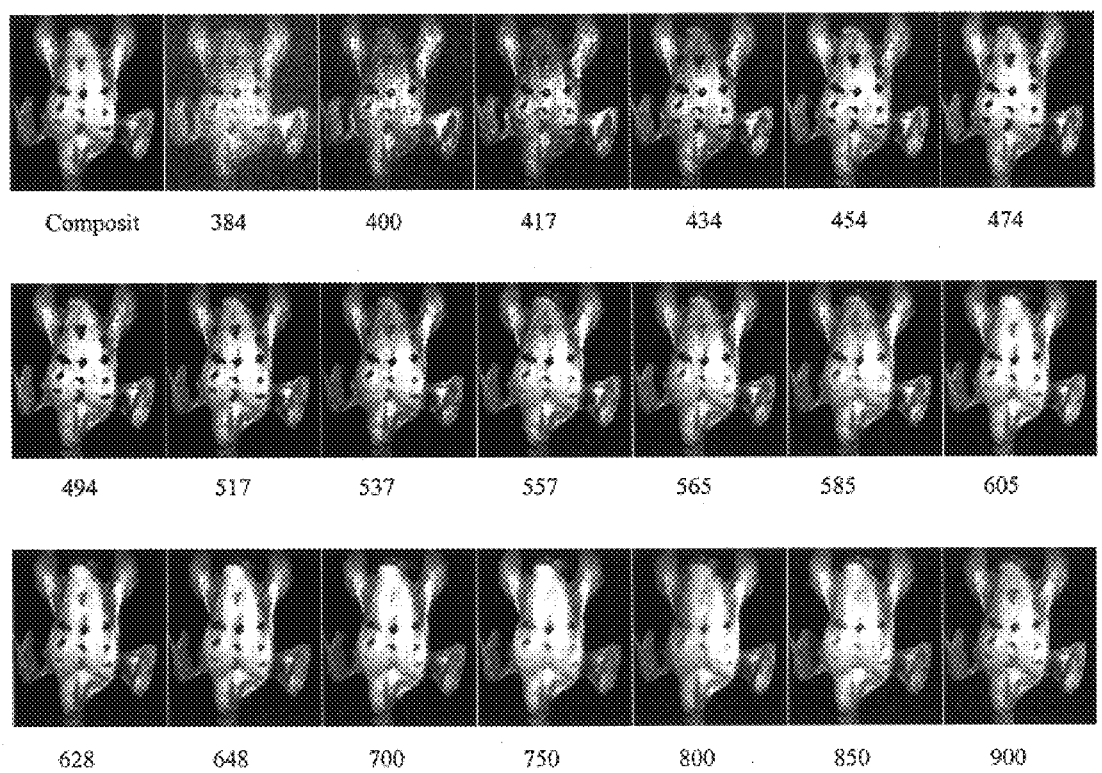
FIG. 9 shows a color composite and images of poultry carcasses contaminated with feces from duodenum, ceca, and colon locations of viscera at selected spectral wavelengths acquired by hyperspectral imaging to demonstrate image quality and spectral-image differences.
Figure 10A:
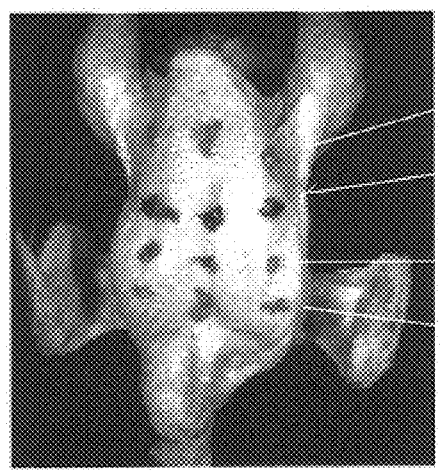
FIGS. 10a–e show a color-composite image (FIG. 10a) and spectral images (FIGS. 10b–e) from image system 10 which correspond to key wavelengths capable of identifying fecal contamination as determined from a Vis/NIR monochromator.
Figure 10B:
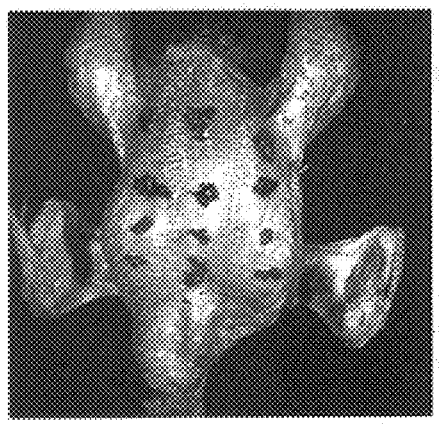
Figure 10C:
Figure 10D:
Figure 10E:
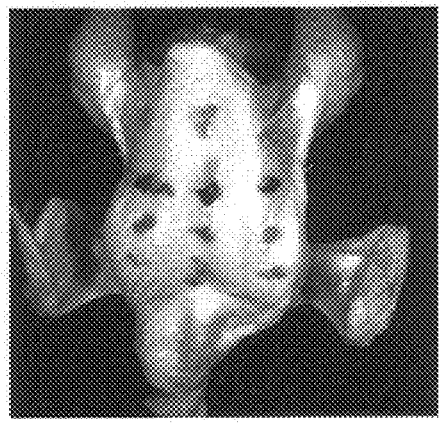

FIG. 9 shows spatial images at some selected spectral wavelengths acquired by the hyperspectral imaging system 10 to demonstrate image quality and spectral differences. The spectral images less than 400-nm wavelengths contained noise compared with others, because the grating diffraction efficiency of the system below about 400 nm is less than about 30% and the nominal spectral range of spectrograph is between about 430 nm to about 900 nm. The fecal (top three rows on carcass) and ingesta spots (bottom row on carcass) on each carcass were displayed distinctively up to about 517 nm. However, the spots of duodenum and ingesta began to disappear as the wavelengths increased beyond 517 nm. Feces from the ceca were clearly found over all the wavelength spectral images. Thus, spectral images selected from hypercube image data were useful for the identification of feces and ingesta contamination on the poultry carcasses.

EXAMPLE 5

Using the wavelength calibration from example 3, the key wavelengths of about 434 nm, 517 nm, 565 nm, and 628 nm, identified with the Vis/NIR monochromator, corresponded to band numbers 58, 143, 190, and 251. FIGS. 10a–e show an approximate color composite (Red: 634 nm; Green: 520 nm; Blue: 446 nm) image and four spectral images at key wavelengths (434, 517, 565, and 628 nm) of a poultry carcass contaminated with feces (duodenum, ceca, colon) and ingesta. Cecal feces were detected from the raw spectral images from the four selected wavelengths including the false color image. However, it was difficult to detect feces from duodenum and ingesta samples with the about 565 nm and about 628 nm spectral images. With a single wavelength image, uncontaminated dark areas in the leg and wing folds were incorrectly identified as contaminates.

Figure 11A:
FIGS. 11a–f show the ratio images at key wavelengths that identify feces (duodenum, ceca, and colon) and ingesta contaminants on a poultry carcass.
Figure 11B:
Figure 11C:
Figure 11D:
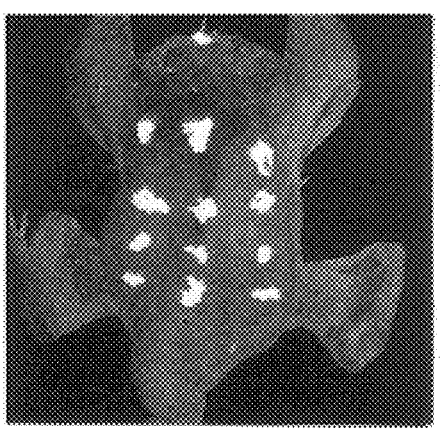
Figure 11E:
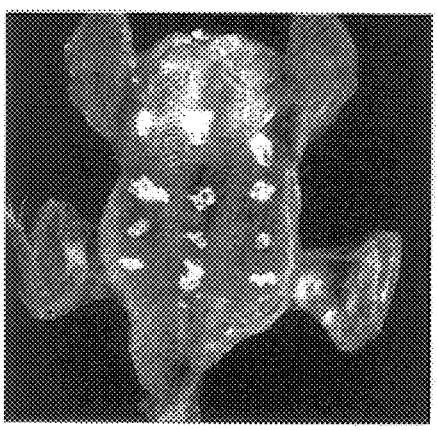
Figure 11F:
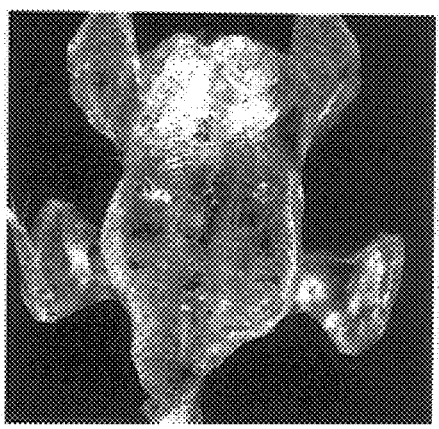

Two wavelength ratio images were determined from the four key wavelengths above. Six ratio images were obtained from the combination of different key wavelengths as shown in FIGS. 11a–f. Among ratio images, the image at 565 nm divided by the image at 517 nm could identify feces (duodenum, ceca, and colon) and ingesta contaminants including colon feces located below the tail as shown in FIG. 11d. The ratio images of the image at 517 nm divided by the image at 434 nm (FIG. 11a), the image at 565 nm divided by the image at 434 nm (FIG. 11b), and the image at 628 nm divided by the image at 434 nm (FIG. 11c) show distinctive ceca (dark spots on the body) contamination. However, other contaminated spots of duodenum, colon, and ingesta were not readily apparent. Even though the image at 628 nm divided by the image at 517 nm (FIG. 11e) shows all the contaminated spots on the body, other white spots under the wings and the area between the legs caused false positive errors. Similarly, as seen on the image at 628 nm divided by the image at 565 nm (FIG. 11f), false positive contamination between the carcass legs were actually caused by skin cuticle or blood hemorrhages on the skin of the carcass.

Figure 12A:
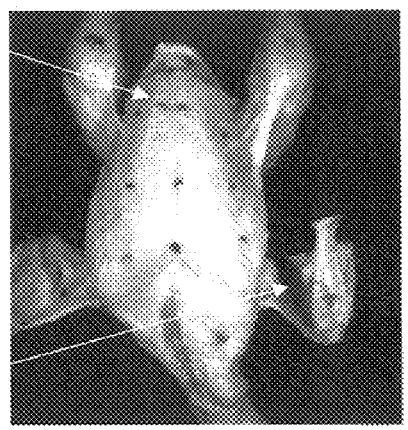
FIG. 12a shows a hyperspectral color-composite image for the identification of fecal and ingesta contaminants on a poultry carcass. The image shows blood hemorrhage (#12a.1) and fecal contaminant in the wing shadow (#12a.2).
Figure 12B:
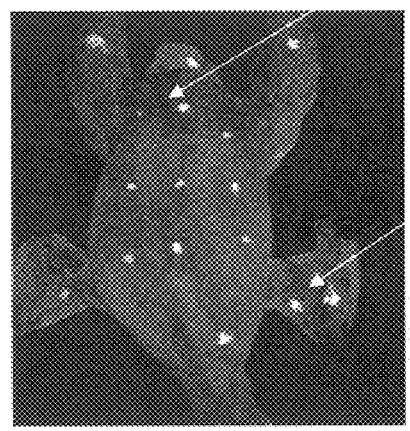
FIG. 12b shows a ratio image (565-nm image divided by 517-nm image) for the identification of fecal and ingesta contaminants on a poultry carcass. The blood hemorrhage (#12b.1) is not identified while the fecal contaminant in the wing shadow (#12b.2) can be identified easily.

Other contaminated carcasses showed this algorithm could detect contaminates of different sizes at different locations. As shown in FIG. 12, blood clot (FIG. 12, 12a.1) in the color composite disappeared (FIG. 12, 12b.1) after the image ratio algorithm was applied. In addition, this algorithm could detect fecal contaminant in the shadow of the wing fold (FIG. 12, 12a.2) in the composite image; (FIG. 12, 12b.2 in the ratio image). Thus, image-ratio algorithm, particularly 565-nm and 517-nm wavelengths, identified fecal and ingesta contaminants on the surface of poultry carcasses extremely well, while minimizing false positive contaminates.

EXAMPLE 6

Figure 13A:
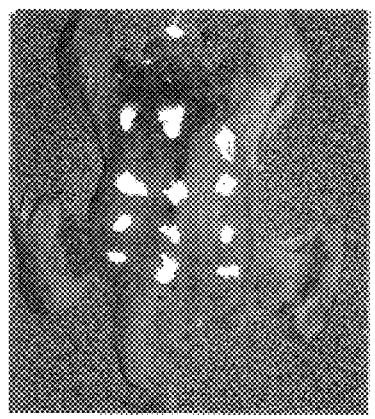
FIGS. 13a, b, and c are ratio images to show a masking procedure to eliminate background noise from algorithm-processed images.
Figure 13B:
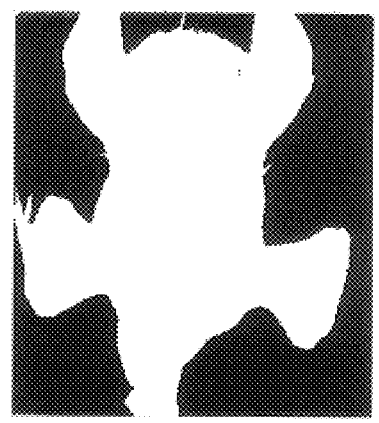
FIG. 13b shows a masking template from a image at 565 nm.
Figure 13C:
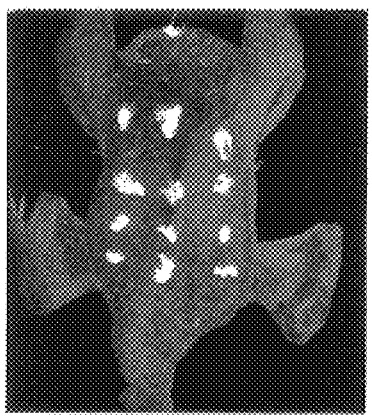
FIG. 13c shows the image of FIG. 13a after the masking template (FIG. 13b) was applied.

The background of the original two-wavelength ratio image is noisier than the chicken body and contains no useful information. To eliminate the background, a masking procedure was implemented for further processing to segregate the ratio image of a carcass from the background. To build a masking template for each carcass (FIG. 13a), a single spectral image was selected from the 512-hyperspectral images. For example, a template (FIG. 13b) was created by thresholding an image at 565 nm. Intensities below a minimum thresholding value of about 120, which corresponded to the background, were then assigned a value of zero. FIG. 13c shows the ratio image after the masking procedure was applied. It was obvious that the masking procedure made the spots of contamination on the carcass more visually distinctive.

EXAMPLE 7

Figure 14A:
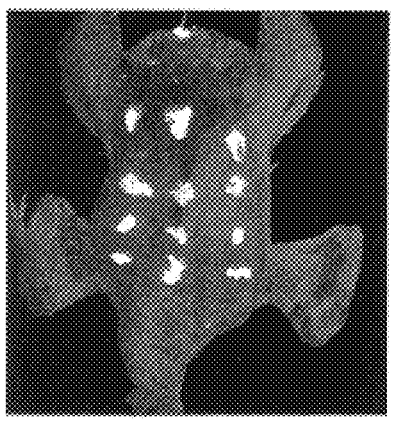
FIGS. 14a–b show a ratio image (565-nm image divided by 517-nm image) before and after histogram stretching of the masked ratio image to qualitatively demonstrate the effectiveness of the histogram stretching routine.
Figure 14B:
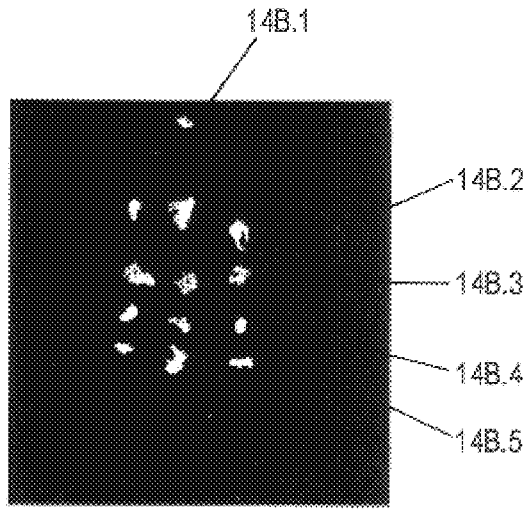
Figure 15A:
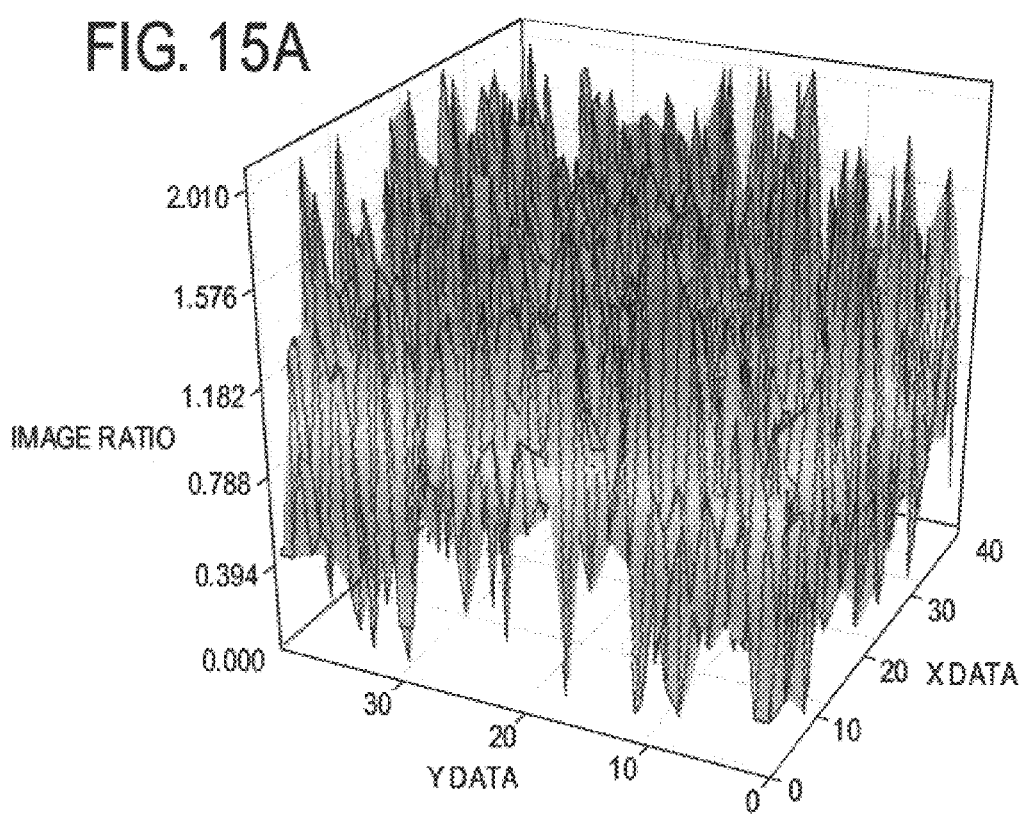
FIGS. 15a–f show graphs of contaminated and uncontaminated poultry carcasses for validation of the ratio-image algorithm before and after the masking and threshold procedures for identification of fecal and ingesta contamination. The figure shows a clean carcass (FIG. 15a), clean carcass with masking procedure applied to eliminate background (FIG. 15b), clean carcass after masking and threshold procedures (FIG. 15c), carcass with contaminant (FIG. 15d), contaminated carcass with masking procedure applied to eliminate background (FIG. 15e), and contaminated carcass after masking and threshold procedures (FIG. 15f).
Figure 15B:
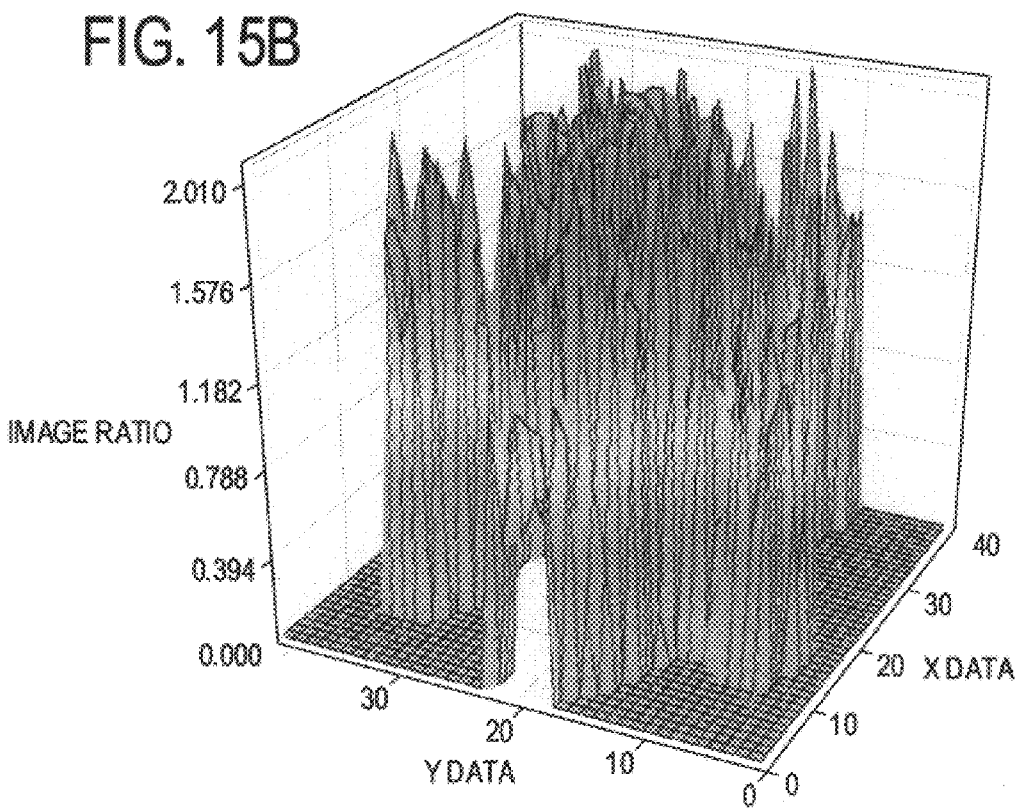
Figure 15C:
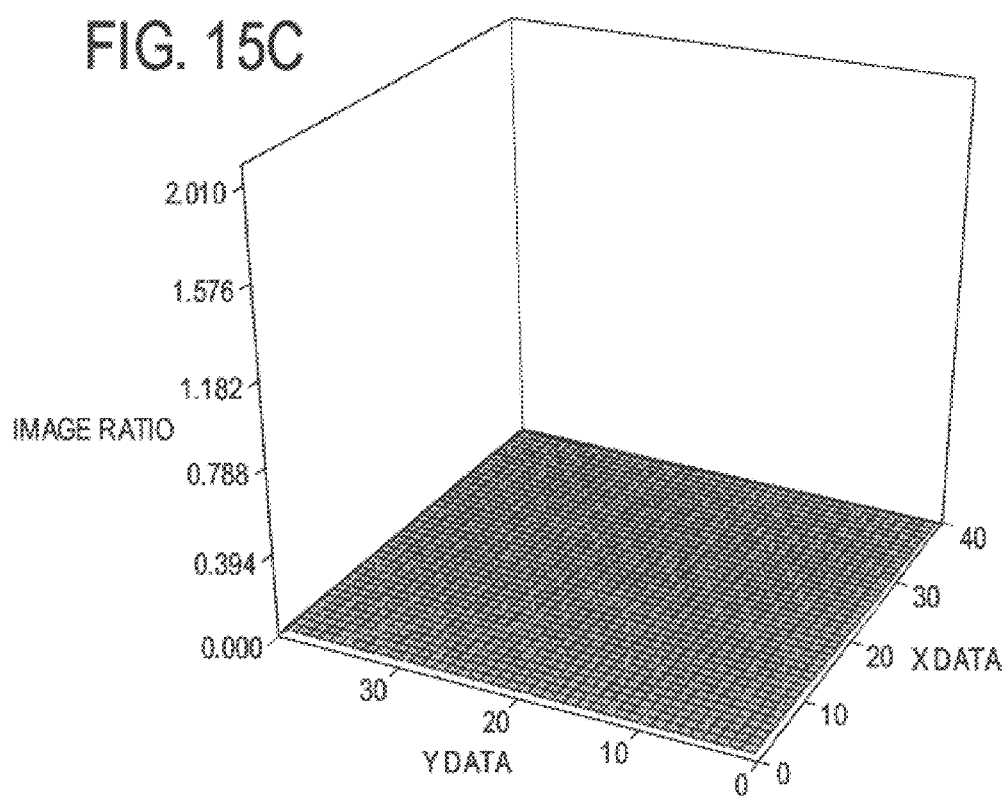
Figure 15D:
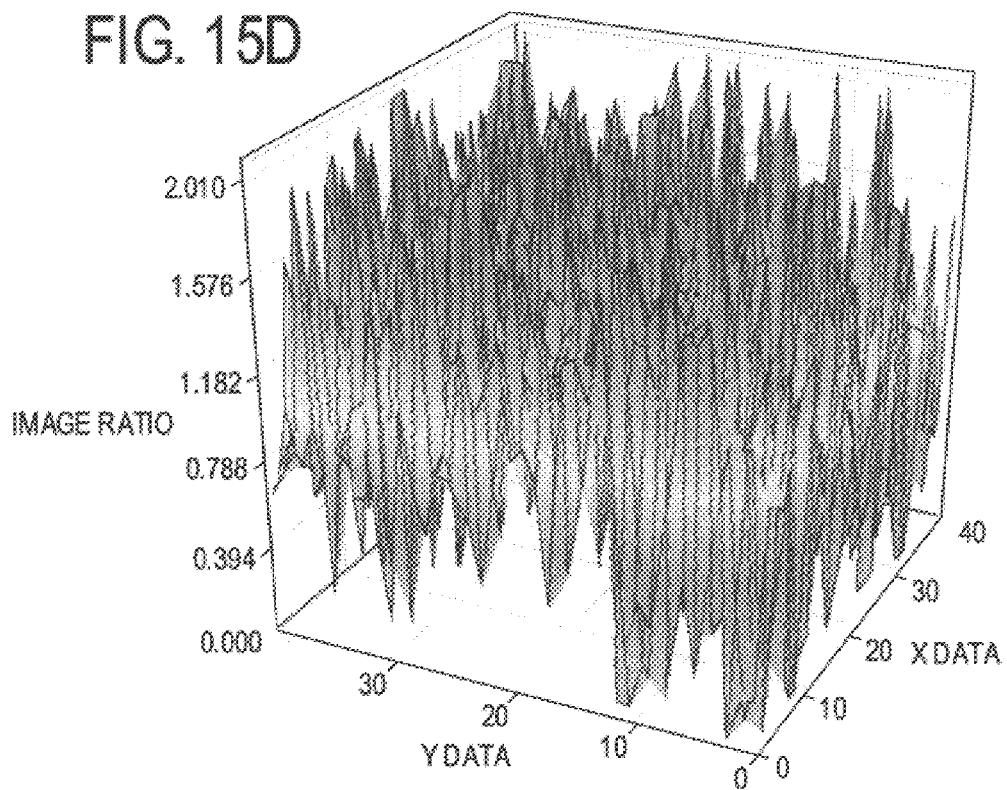
Figure 15E:
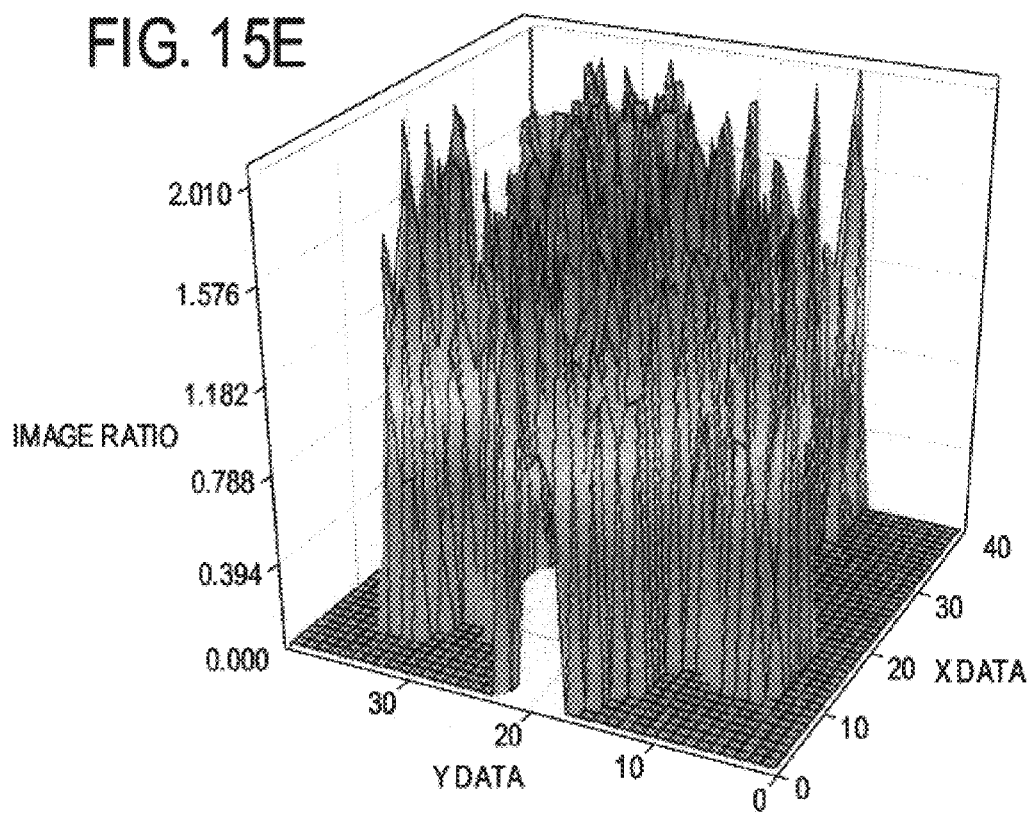
Figure 15F:
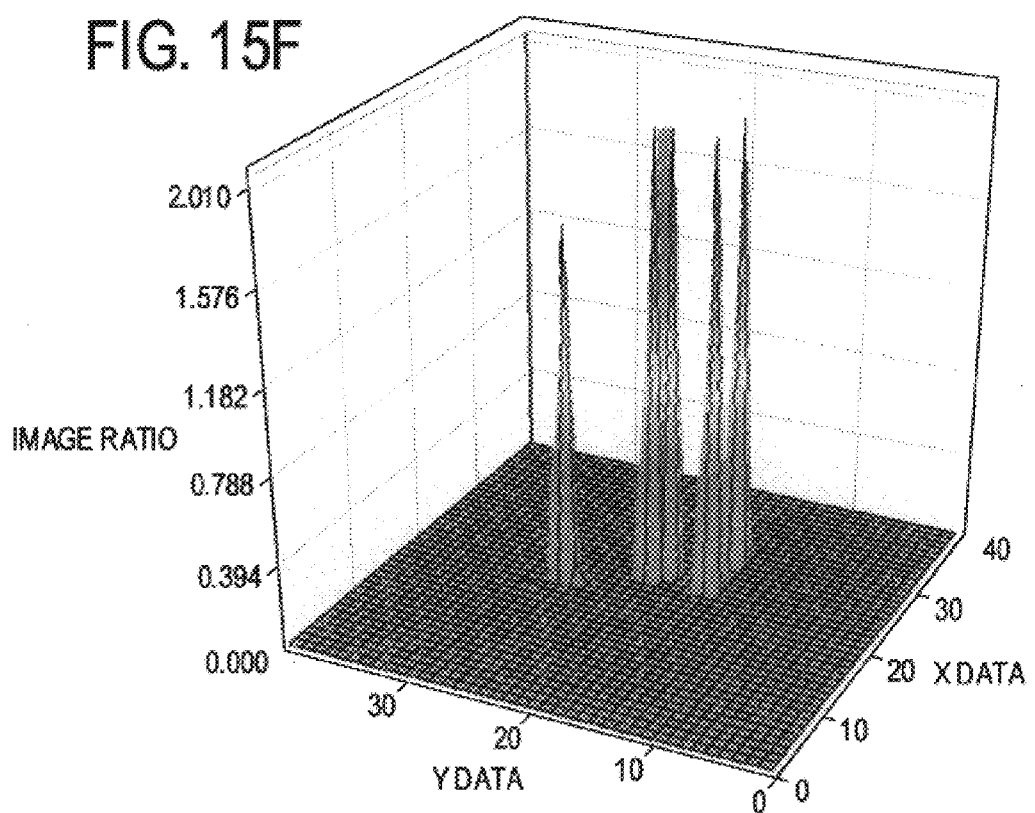

After eliminating the background noise with a masking procedure, a histogram stretching algorithm was used to separate feces and ingesta contaminates from a carcass as shown in FIG. 14a. Both linear and nonlinear histogram-stretching algorithms were tested. As shown in FIG. 14b, top center white portion of vent area indicates natural contamination of colon feces (FIG. 14, 14b.1); the second row represents duodenum (FIG. 14, 14b.2); third row represents ceca (FIG. 14, 14b.3); fourth row represents colon feces (FIG. 14, 14b.4); and fifth row represents ingesta contaminates (FIG. 14, 14b.5), respectively. From numerous ratio images of both hard and soft scalded carcasses, parameter values of histogram-stretching algorithm for the sample in FIGS. 14a and 14b were determined as follows: minimum input=about 1.28; maximum input=about 1.60; minimum output=about 0.75; maximum output=about 2.38. These parameter values force intensities below 1.28 to have a display value of zero, intensities between 1.28 and 1.60 to have display values that linearly vary from zero to full scale, and intensities above 1.60 to have display values at full scale.

EXAMPLE 8

The hyperspectral image processing algorithms (ratio of two-wavelength images) demonstrated in the previous examples were tested with sixteen poultry carcasses. As shown in Table 2 below, the histogram stretching algorithms were accurate for both the linear and nonlinear models. Even though threshold values of each sample varied slightly, the mean minimum and maximum input threshold values were about 0.76 (Standard Deviation (S.D.)=about −0.03) and about 2.29 (S.D.=about 0.25). For the linear model, the mean minimum and maximum values were about 1.25 (S.D.=about 0.05) and about 1.69 (S.D.=about 0.08), respectively. For the square-root model, the mean minimum and maximum values were about 1.39 (S.D.=about 0.06) and about 1.55 (S.D.=about 0.13), respectively.

The square-root model of histogram stretching performed perfectly for identifying fecal and ingesta contaminants. However, the linear model missed several contaminant spots (chicken sample #2, #3, and #7).

EXAMPLE 9

FIG. 15 shows the comparison of intensity distribution between a clean and contaminated carcass to demonstrate the performance of the masking procedure and the threshold algorithm. As shown in FIGS. 15a–e, there were no readily apparent differences of the intensity distribution of the original ratio images between the clean (FIG. 15a) and fecal and ingesta contaminated (FIG. 15d) carcass. Masking makes the carcass outline apparent (FIGS. 15b and 15e), but little distinctive between the contaminated and uncontaminated carcass can be seen. After the thresholding algorithm was applied, intensities above the threshold are shown in FIG. 15c for the clean bird disappeared; whereas the peak intensities above the threshold in FIG. 15f indicated the spots of feces and ingesta on the carcass. Therefore, the threshold algorithm can be further applied for the automatic detection of fecal and ingesta contaminants on poultry carcasses in conjunction with masking and the optimum threshold parameter values.

The foregoing detailed description is for the purpose of illustration. Such detail is solely for that purpose and those skilled in the art can make variations therein without departing from the spirit and scope of the invention.

Index of the Elements

1A. Charge-Coupled Device Detector
1B. Lens Assembly
1C. Spectrograph
2. Lighting System
2A. Fiber Optic Cable
2B. Lamp Assembly
2C. Power Supply for Lighting
4. Power Supply for at least one Charge-Coupled Device Detector
5. Battery Backup
6. Computer Monitor
7. Computer
7A. Interface Cable
9. Data Processing Unit

TABLE 2

Threshold values of histogram stretching for segregating feces and ingesta from chicken carcasses.

| | Input | | Output | | | | Number of Contaminants | |
| | | | Linear | | Square root | | Predicted | |
| Sample ID | Min. | Max. | Lower | Upper | Lower | Upper | Linear/Square | Actual |
|---|---|---|---|---|---|---|---|---|
| Chicken#1 | 0.77 | 2.62 | 1.20 | 1.88 | 1.34 | 1.38 | 9/9 | 9 |
| Chicken#2 | 0.77 | 2.03 | 1.28 | 1.80 | 1.38 | 1.46 | 8/9 | 9 |
| Chicken#3 | 0.76 | 2.22 | 1.20 | 1.80 | 1.30 | 1.94 | 7/9 | 9 |
| Chicken#4 | 0.72 | 2.28 | 1.26 | 1.60 | 1.36 | 1.56 | 10/10 | 10 |
| Chicken#5 | 0.80 | 2.10 | 1.20 | 1.70 | 1.36 | 1.46 | 9/9 | 9 |
| Chicken#6 | 0.75 | 2.33 | 1.28 | 1.60 | 1.36 | 1.46 | 11/11 | 11 |
| Chicken#7 | 0.74 | 2.01 | 1.26 | 1.60 | 1.30 | 1.40 | 6/8 | 8 |
| Chicken#8 | 0.80 | 2.30 | 1.20 | 1.70 | 1.46 | 1.56 | 12/12 | 12 |
| Chicken#9 | 0.74 | 2.46 | 1.30 | 1.70 | 1.50 | 1.60 | 14/14 | 14 |
| Chicken#10 | 0.74 | 2.06 | 1.34 | 1.70 | 1.46 | 1.56 | 16/16 | 16 |
| Chicken#11 | 0.76 | 2.14 | 1.20 | 1.64 | 1.41 | 1.51 | 16/16 | 16 |
| Chicken#12 | 0.74 | 2.51 | 1.30 | 1.64 | 1.44 | 1.57 | 14/14 | 14 |
| Chicken#13 | 0.73 | 2.18 | 1.20 | 1.68 | 1.40 | 1.50 | 13/13 | 13 |
| Chicken#14 | 0.80 | 2.96 | 1.30 | 1.66 | 1.36 | 1.50 | 12/12 | 12 |
| Chicken#15 | 0.80 | 2.13 | 1.28 | 1.60 | 1.40 | 1.60 | 12/12 | 12 |
| Chicken#16 | 0.73 | 2.34 | 1.20 | 1.74 | 1.44 | 1.66 | 16/16 | 16 |
| Mean | 0.76 | 2.29 | 1.25 | 1.69 | 1.39 | 1.55 | | |
| Std. Dev. | 0.03 | 0.25 | 0.05 | 0.08 | 0.06 | 0.13 | | |

10. Imaging Systems
12. Means for Obtaining Spectral Images
17. Frame Grabber
19. Software
20. Algorithm

We claim:

1. An imaging system for determination of contamination on food comprising:
 at least one charge-coupled device detector with an optical filter capable of collecting at least two discrete narrow-band images,
 a lighting system,
 a data processing unit operatively connected to said detectors for receiving images for analysis of the spectral properties of an image created by said detector, and
 a computer readable memory encoded with a computer program containing a detection algorithm based on mathematical analysis of selected key wavelengths of radiation detected by said detector wherein said selected key wavelengths are derived by using a calibration process including:
 (a) collecting spectra with a visible/near infrared monochromator by irradiating samples of uncontaminated food and pure contaminants representative of the types of contamination to be determined with visible/near infrared radiation and digitally recording reflectance intensity from about 400 nm to about 2500 nm in about 2-nm intervals,
 (b) transforming said spectra recorded in step (a) for each sample to $\log_{10}$, spectra in absorbence units,
 (c) transforming said $\log_{10}$ spectra with standard normal variate and detrending procedures to remove interferences of scatter, particle size, and variations in baseline shift and curvilinearity,
 (d) processing said transformed spectra in step (c) with at least one of Principal Component Analysis and Partial Least Squares regression for formation of scores and loadings,
 (e) comparing said scores with variations in Principal Components for selecting discrete Principal Components at which scores correlate with uncontaminated foods and contaminants,
 (f) evaluating loadings of said discrete Principal Components for extreme variations in absolute value to identify key wavelengths,
 (g) selecting images at key wavelengths identified in step f, and
 (h) calculating algorithm to detect contaminants.

2. The imaging system of claim 1 wherein said optical filter is selected from the group consisting of a line-scan spectrograph, a liquid crystal tunable filter, an acousto-optic tunable filter, and a narrow band-pass filter; wherein said filters are capable of collecting at least two discrete spectral images each taken at a different wavelength.

3. A method for identifying contamination on food comprising:
 (a) identifying key wavelengths by performing the following steps:
  (i) preparing samples of uncontaminated and pure contaminants representative of the types of contamination to be determined,
  (ii) collecting spectra of said samples,
  (iii) transforming spectra of said samples to $\log_{10}$ in absorbence units,
  (iv) transforming said $\log_{10}$ spectra with standard normal variate and detrending procedures to remove interferences of scatter, particle size, and variations in baseline shift and curvilinearity,
  (v) processing said transformed spectra in step (iv) with at least one of Principle Component Analysis and Partial Least Squares regression for formation of scores and loadings,
  (vi) comparing said scores with variations in Principal Components for selecting discrete Principal Components at which scores correlate with uncontaminated foods and contaminants,
  (vii) evaluating loadings of said discrete principal components for extreme variations in absolute value for identifying key wavelengths,
  (viii) identifying said key wavelengths based on the results of step (vii),
 (b) calibrating image wavelengths wherein said calibration includes selecting sensor binning to determine band numbers, imaging known wavelength standards to identify wavelength peaks and band numbers, performing a non-linear regression on said wavelengths against said band numbers, and applying said regression to subsequent images,
 (c) creating hyperspectral or multispectral images of said samples,
 (d) selecting said images at said key wavelengths based on the results of step (viii),
 (e) applying algorithms using key wavelengths identified in step (viii) to form an image dataset for the identification of contamination.

4. A method for identifying contamination on food comprising:
 (a) identifying key wavelengths by performing the following steps:
  (i) preparing samples of uncontaminated and pure contaminants representative of the types of contamination to be determined,
  (ii) collecting spectra of said samples,
  (iii) transforming spectra of said samples to $\log_{10}$ in absorbence units,
  (iv) transforming said $\log_{10}$ spectra in absorbence units,
  (v) processing said transformed spectra in step (iv) with at least one of Principle Component Analysis and Partial Least Squares regression for formation of scores and loadings,
  (vi) comparing said scores with variations in Principal Components for selecting discrete Principal Components at which scores correlate with uncontaminated foods and contaminants,
  (vii) evaluating loadings of said discrete principal components for extreme variations in absolute value for selecting key wavelengths,
  (viii) identifying key wavelengths based on the results of step (vii),
 (b) calibrating image wavelengths wherein said calibration includes selecting sensor binning to determine band numbers, imaging known wavelength standards to identify wavelength peaks and band numbers, performing a non-linear regression on said wavelengths against said band numbers, and applying said regression to subsequent images,
 (c) creating hyperspectral or multispectral images of said samples,
 (d) selecting said images at said key wavelengths based on the results of step (viii),
 (e) calculating a ratio of two images at said two wavelengths to form a ratio image, (f) performing a masking procedure on said ratio image to reduce background noise, (g) applying histogram stretching to said ratio image to qualitatively identify contaminants in real-time, and/or (h) applying thresholding to said ratio image from step f to quantitatively identify contaminants in real-time.

5. The method of claim 4 further including transforming said log10 spectra with standard normal variate and detrending procedures to remove interference of scatter, particle size, and variations in baseline shift and curvilinearity.

6. The method of claim 4 wherein hyperspectral images are collected by a line-scan spectrograph with a charge-coupled detector.

7. The method of claim 4 wherein multispectral images are collected using an imaging device selected from the group consisting of a common aperture camera with at least two charge-coupled device detectors, at least one charge-coupled device detector with a liquid crystal tunable filter, at least one charge-coupled device with an acousto-optic tunable filter, at least one charge-coupled device with a line-scan spectrograph, and multiple charge-coupled device detectors with narrow band-pass filters.

8. The method of claim 4 wherein said ratio image is determined by dividing an image at a first key wavelength by an image at a second key wavelength on a pixel by pixel basis of said collected images from step (4d).

9. A method comprising:

(a) preparing samples of uncontaminated food and pure contaminants representative of the types of contamination to be determined, (b) collecting spectra of said samples, (c) transforming spectra of said samples to $\log_{10}$ spectra in absorbence units, (d) processing said transformed spectra in step (c) with at least one of Principal Component Analysis and Partial Least Squares regression for formation of scores and loadings, (e) comparing said scores with variations in Principal Components for selecting discrete Principal Components at which scores correlate with uncontaminated foods and contaminants, (f) evaluating loadings of said discrete principal components for extreme variations in absolute value for selecting key wavelengths, and (g) identifying key wavelengths for identification of contaminants based on the results of step (f).

10. A process for detecting contamination on food comprising:

(a) illuminating said food with a source of electromagnetic radiation having a predetermined spectral content, (b) detecting radiation from said source reflected by said food item in each of four predetermined wavelengths $\lambda_1, \lambda_2, \lambda_3, \lambda_4$, and generating a first data set comprising digital values indicative of reflected radiation intensity in each of said wavelengths;

(c) processing said digital values according to an algorithm as follows $$I = \frac{(\lambda_1 - n)(\lambda_3 + \lambda_4)}{\lambda_3(\lambda_1 + \lambda_2)}$$

wherein n is a constant integer; and
I is an indication of fecal contamination.

11. The process of claim 10 wherein
$\lambda_1$ is from about 750 to about 830 nm,
$\lambda_2$ is from about 450 to about 500 nm,
$\lambda_3$ is from about 500 to about 535 nm,
$\lambda_4$ is from about 550 to about 585 nm.

12. The process of claim 10 further comprising calculating, for each digital value in said first data set, mean and variance values, based on a set of proximate digital values, thereby creating a mean value data set and a variance value data set;

adding said mean value and variance value data sets to create a final data set;

determining presence or absence of contamination based on values in said final data set.

13. The process of claim 12 wherein said determining step comprises:

comparing data values in said final data set to a predetermined threshold value; and determining presence of contamination based on results of said contamination.

14. A process for detecting contamination on food comprising:

(a) illuminating said food with a source of electromagnetic radiation having a predetermined spectral content;

(b) detecting radiation from said source reflected by said food in a plurality of predetermined wavelengths and generating a data set comprising signals indicative of reflected radiation intensity in each of said wavelengths;

(c) processing said data set according to a predetermined mathematical function to generate a plurality of rule files comprising respective image files;

(d) combining said rule files to generate a combined data set;

(e) performing a texture analysis on said combined data set to generate spatially distributed mean and variance data;

(f) summing said mean and variance data to yield output data; and (g) detecting contamination based on said output data.

15. The process of claim 14 wherein said predetermined mathematic function is defined by:

$$\cos^{-1}\left(\frac{\sum_{i=1}^{nb} t_i r_i}{\left(\sum_{i=1}^{nb} t_i^2\right)^{1/2} \left(\sum_{i=1}^{nb} r_i^2\right)^{1/2}}\right)$$

wherein
nb=number of said predetermined wavelengths;
t=detected reflected radiation value from said food for a defined wavelength; and
<r=reflectance value of a contaminant at said defined wavelength.

16. A method for determining contamination on poultry or livestock carcasses comprising:

(a) obtaining poultry or livestock carcasses for which contaminants are to be determined, (b) creating hyperspectral or multispectral images of said carcasses, (c) selecting images at key wavelength, (d) applying an algorithm to detect contaminants from images selected in step (c), (e) applying masking to reduce background noise in images of step (d), (f) applying histogram stretching to images of step (e) to qualitatively identify contaminants, and (g) applying thresholding to images of step (e) or (f) to quantitatively identify contaminants in real-time.

17. The method of claim 16 wherein said algorithms are selected from the group consisting of a ratio of key wavelengths and a linear combination of key wavelengths.

18. A computer readable medium encoded with a computer program for detecting contamination on food by causing a computer to process image signals indicative of intensity of radiation reflected from said food in four wavelengths $\lambda_1$–$\lambda_4$, using an algorithm:

$$I = \frac{(\lambda_1 - n)(\lambda_3 + \lambda_4)}{\lambda_3(\lambda_1 + \lambda_2)}$$

a wherein I is an indication of contamination.

19. An apparatus for detecting contamination on food comprising:

(a) a plurality of sensors for detecting spatially distributed radiation reflected from a food at four wavelengths $\lambda_1$, $\lambda_2$, $\lambda_3$, and $\lambda_4$, and generating image signals indicative thereof;

a computer; and a computer readable medium coupled to said computer for causing said computer to process said image signals using an algorithm:

$$I = \frac{(\lambda_1 - n)(\lambda_3 + \lambda_4)}{\lambda_3(\lambda_1 + \lambda_2)}$$

wherein I is an indication of contamination.

20. A computer readable medium encoded with a computer program for detecting contamination on a food by causing a computer to process spectrally resolved image information indicative of intensity of radiation reflected from said food in a plurality of wavelength by performing the following steps:

(a) calculating data sets in the form of rule files, using said spectrally resolved image information, comprising values of $\alpha$ wherein $$\alpha = \cos^{-1}\left(\frac{\sum_{i=1}^{nb} t_i r_i}{\left(\sum_{i=1}^{nb} t_i^2\right)^{1/2}\left(\sum_{i=1}^{nb} r_i^2\right)^{1/2}}\right)$$

wherein nb=number of bands of spectrally resolved image information;

t=detected spectrally resolved image information values for an $i_{th}$ band; and r=spectrally resolved image information value for an $i_{th}$ band for a contaminant whose presence is to be detected.

(b) combining said rule files to generate a combined data set;

(c) performing a texture analysis on said combined data set to generate spatially distributed mean and variance data; and (d) summing said mean and variance data to yield output data indicative of contamination.

21. An apparatus for detecting contamination on food comprising:

(a) a plurality of sensors for detecting spatially distributed spectrally resolved image information indicative of intensity radiation reflected from a food in a plurality of wavelength bands;

(b) a computer readable medium coupled to said computer for causing said computer to process said image signals by calculating data sets in the form of Rule Files, using said spectrally resolved image information, using a formula $$\alpha = \cos^{-1}\left(\frac{\sum_{i=1}^{nb} t_i r_i}{\left(\sum_{i=1}^{nb} t_i^2\right)^{1/2}\left(\sum_{i=1}^{nb} r_i^2\right)^{1/2}}\right)$$

wherein nb=number of bands of spectrally resolved image information;

t=detected spectrally resolved image information values for an $i_{th}$ band, and r=spectrally resolved image information value for an $i^{th}$ band for a contaminant whose presence is to be detected;

(c) combining said Rule Files to generate a combined data set;

(d) performing a texture analysis on said combined data set to generate spatially distributed mean and variance data; and (e) summing said mean and variance data to yield output indicative of contamination.

* * * * *